United States Patent
Traxler et al.

[11] Patent Number: 6,140,332
[45] Date of Patent: Oct. 31, 2000

[54] PYRROLOPYRIMIDINES AND PROCESSES FOR THE PREPARATION THEREOF

[75] Inventors: Peter Traxler, Schönenbuch; Guido Bold, Gipf-Oberfrick, both of Switzerland; Wolfgang Karl-Diether Brill, Schopfheim, Germany; Jörg Frei, Hölstein, Switzerland

[73] Assignee: Novartis AG, Basel, Switzerland

[21] Appl. No.: 08/981,877

[22] PCT Filed: Jun. 24, 1996

[86] PCT No.: PCT/EP96/02728

§ 371 Date: Jan. 26, 1998

§ 102(e) Date: Jan. 26, 1998

[87] PCT Pub. No.: WO97/02266

PCT Pub. Date: Jan. 23, 1997

[30] Foreign Application Priority Data

| Jul. 6, 1995 | [CH] | Switzerland | 1976/95 |
| Sep. 1, 1995 | [CH] | Switzerland | 2498/95 |
| Nov. 10, 1995 | [CH] | Switzerland | 3198/95 |
| Feb. 1, 1996 | [CH] | Switzerland | 255/96 |
| May 13, 1996 | [CH] | Switzerland | 1224/96 |

[51] Int. Cl.⁷ ........................ A61K 31/519; C07D 487/04
[52] U.S. Cl. .................... 514/258; 514/267; 514/252.16; 544/250; 544/251; 544/280
[58] Field of Search .................... 544/250, 251, 544/280; 514/267, 258, 253, 252.16

[56] References Cited

U.S. PATENT DOCUMENTS

| 3,037,980 | 6/1962 | Hitchings et al. | 260/256.4 |
| 5,674,998 | 10/1997 | Boyer et al. | 536/27.13 |
| 5,679,683 | 10/1997 | Bridges et al. | 514/267 |

FOREIGN PATENT DOCUMENTS

| 682 027 | 11/1995 | European Pat. Off. |
| 773 023 A1 | 5/1997 | European Pat. Off. |
| 795 556 A1 | 9/1997 | European Pat. Off. |
| 3036390 | 5/1982 | Germany |
| WO 92/20642 | 11/1992 | WIPO |
| WO 95 19774 | 7/1995 | WIPO |
| WO 95 19970 | 7/1995 | WIPO |
| 96/10028 | 4/1996 | WIPO |
| 96/31510 | 10/1996 | WIPO |
| WO 96/40142 | 12/1996 | WIPO |

OTHER PUBLICATIONS

Traxler et al., "4–(Phenylamino)pyrrolopyrimidines: Potent and Selective, ATP Site Directed Inhibitors of the EGF–Receptor Protein Tyrosine Kinase," J. Med. Chem., vol. 39, pp. 2285–2292, Jun. 7, 1996.
R.L. Dow et al., 209th ACS meeting held Apr. 2–6 or 7 (1995).
L.Sun et al., 209th ACS meeting held Apr. 2–6 or 7 (1995).
A.J.Bridges et al., 86th Annual meeting of the Amer.Assoc.of Cancer Res. held Mar. 18–22 (1995).
J.P. Marquet et al., Chimica Therapeutica, No. 6, pp. 427–438 (1971).*
R.J. Mattson, et al., Synthesis, No. 3, pp. 217–218 (1979).*
Liebigs Ann. Chem. pp. 2066–2072 (1983).
Liebigs Ann. Chem. pp. 142–148 (1985).
J. Heterocyclic Chem., vol. 22, pp. 859–863 (1985).
Derwent Abstract No. 92–213005/26 (1992).

*Primary Examiner*—Richard L. Raymond
*Attorney, Agent, or Firm*—Joseph J. Borovian

[57] ABSTRACT

Described are 7H-pyrrolo[2,3-d]pyrimidine derivatives of formula I

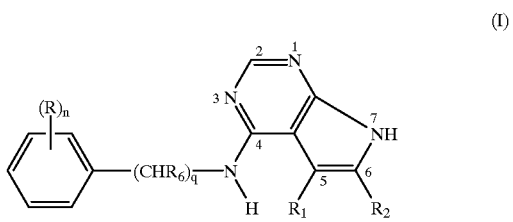

wherein the symbols are as defined in claim 1.

Those compounds inhibit tyrosine protein kinase and can be used in the treatment of hyperproliferative diseases, for example tumour diseases.

25 Claims, No Drawings

PYRROLOPYRIMIDINES AND PROCESSES FOR THE PREPARATION THEREOF

This application is a 371 of PCT/EP96/02728, filed Jun. 24, 1996.

The invention relates to 7H-pyrrolo[2,3-d]pyrimidine derivatives and to processes and novel intermediates for the preparation thereof, to pharmaceutical formulations comprising such derivatives and to the use of those derivatives as medicaments. The invention relates to 7H-pyrrolo[2,3-d] pyrimidine derivatives of formula I

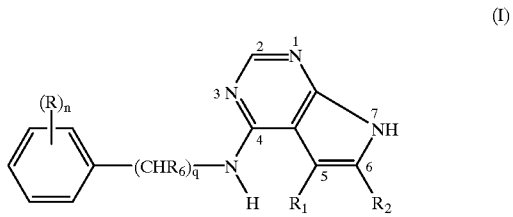

wherein
q is 0 or 1,
n is from 1 to 3 when q is 0, or n is from 0 to 3 when q is 1,
R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or tri-fluoromethyl, it being possible when several radicals R are present in the molecule for those radicals to be identical or different,
a) $R_1$ and $R_2$ are each independently of the other
α) phenyl substituted by carbamoylmethoxy, carboxymethoxy, benzyloxycarbonylmethoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro;
β) hydrogen;
γ) unsubstituted or halo- or lower alkyl-substituted pyridyl;
δ) N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzylcarbamoyl; formyl; lower alkanoyl; lower alkenyl; lower alkenyloxy; or
ε) lower alkyl substituted by
εα) halogen, amino, lower alkylamino, piperazino, di-lower alkylamino,
εβ) phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl,
εγ) hydroxy, lower alkoxy, cyano, carboxy, lower alkoxycarbonyl, carbamoyl, N-lower alkyl-carbamoyl, N,N-di-lower alkyl-carbamoyl, mercapto or
εδ) a radical of the formula $R_3$—S(O)$_m$— wherein $R_3$ is lower alkyl and m is 0, 1 or 2, or
b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or
c) $R_1$ and $R_2$ together are $C_4$–$C_{10}$-1,4-alkadienylene substituted by amino, lower alkanoylamino, lower alkylamino, N,N-di-lower alkylamino, nitro, halogen, hydroxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, or d) when q is 1, $R_1$ and $R_2$ are each independently of the other unsubstituted lower alkyl or unsubstituted phenyl or have one of the meanings given above in paragraph
a), and
$R_6$ is hydrogen, lower alkyl, lower alkoxycarbonyl, carbamoyl, N-lower alkyl-carbamoyl or N,N-di-lower alkyl-carbamoyl,
and to the salts thereof,
with the exception of the compound of formula I wherein n is 0, q is 1, $R_1$ and $R_6$ are each hydrogen and $R_2$ is methyl.

The prefix "lower" used hereinbefore and hereinafter denotes a radical having up to and including a maximum of 7, especially up to and including a maximum of 4, and above all 1 or 2, carbon atoms.

Preferably, n is 2 or especially 1. When there is only one substituent R, that substituent is preferably in the 3-position on the phenyl ring. When two substituents R are present, those substituents are preferably in the 3- and 4-positions.

Halogen R is bromine, iodine or preferably fluorine or chlorine. When n is 1, R is preferably chlorine.

Lower alkyl is, for example, methyl.

Lower alkanoyloxy is, for example, acetoxy.

Lower alkoxy is, for example, methoxy.

Lower alkoxycarbonyl is, for example, methoxycarbonyl.

N-Lower alkyl-carbamoyl is, for example, N-methyl-carbamoyl, N-(n-butyl)-carbamoyl or N-(3-methyl-but-1-yl)-carbamoyl.

N,N-Di-lower alkyl-carbamoyl is, for example, N,N-dimethyl-carbamoyl.

Lower alkanoylamino is, for example, acetylamino.

Lower alkylamino is, for example, methylamino.

N,N-Di-lower alkylamino is, for example, dimethylamino.

Lower alkoxycarbonyl-methoxy is, for example, methoxycarbonyl-methoxy.

Substituted phenyl $R_1$ or $R_2$ may carry one or more, but preferably not more than three, substituents which may be identical or different. Substituted phenyl $R_1$ or $R_2$ preferably carries only one substituent which may be in the ortho-, the meta- or, preferably, the para-position.

Phenyl-substituted phenyl $R_1$ or $R_2$ is, for example, biphenylyl, preferably 4-biphenylyl.

Pyridyl is, for example, 2-pyridyl.

Halogen in a radical $R_1$ or $R_2$ is fluorine, bromine, iodine or preferably chlorine.

Naphthyl is, for example, 2-naphthyl.

Lower alkenyl is, for example, vinyl, prop-1-enyl or prop-2-enyl (allyl).

Lower alkenyloxy is, for example, vinyloxy, prop-1-enyloxy or prop-2-enyloxy (allyloxy).

Substituted lower alkyl $R_1$ or $R_2$ may carry one or more, but preferably not more than three, substituents, which may be identical or different. Substituted lower alkyl $R_1$ or $R_2$ preferably carries only one substituent.

Lower alkyl $R_1$ or $R_2$ substituted by phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl is especially methyl that is substituted in that manner, for example anilinomethyl or 4-methoxy-anilino-methyl.

$C_4$–$C_{10}$-1,4-Alkadienylene is a divalent buta-1,3-diene radical in which each of terminal carbon atoms Nos. 1 and 4 has a free valency and which can be substituted by lower alkyl, the radical as a whole, however, having not more than 10 carbon atoms, for example buta-1,3-dien-1,4-ylene.

Aza-1,4-alkadienylene having up to 9 carbon atoms is $C_4$–$C_{10}$-1,4-alkadienylene as defined above in which at least one carbon atom, preferably a carbon atom of the butadiene chain, such as especially a terminal carbon atom of the butadiene chain, has been replaced by nitrogen, for example 1-aza-1,4-alkadienylene, such as especially 1-aza-buta-1,3-dien-1,4-ylene. Aza-1,4-alkadienylene preferably contains from 1 to 3 nitrogen atoms, especially only one. 1-Aza-1,4-alkadienylene having only one nitrogen atom is preferably bonded via that nitrogen atom to carbon atom 6 of the 7H-pyrrolo[2,3-d]pyrimidine ring system.

Salts of compounds of formula I are especially acid addition salts with organic or inorganic acids, especially the pharmaceutically acceptable, non-toxic salts. Suitable inorganic acids are, for example, carbonic acid (preferably in the form of the carbonates or hydrogen carbonates); hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcystine, pyruvic acid, acetoacetic acid, phosphoserine, 2- or 3-glycerophosphoric acid, glucose-6-phosphoric acid, glucose-1-phosphoric acid, fructose-1,6-bis-phosphoric acid, maleic acid, hydroxymaleic acid, methylmaleic acid, cyclohexanecarboxylic acid, adamant-anecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid. Compounds of formula I having at least one free carboxy group are capable of forming internal salts or metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

For isolation or purification purposes it is also possible to use pharmaceutically unacceptable salts, for example picrates or perchlorates. Only salts that are pharmaceutically acceptable and non-toxic (at the appropriate dosages) are used therapeutically and those salts are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable pharmacologically useful properties. In particular they exhibit specific inhibitory activities that are of pharmacological interest. They are effective especially as tyrosine protein kinase inhibitors and/or (furthermore) as inhibitors of serine/threonine protein kinases; they exhibit, for example, powerful inhibition of the tyrosine kinase activity of the receptor for epidermal growth factor (EGF) and of c-erbB2 kinase. Those receptor-specific enzyme activities play a key role in signal transmission in a large number of mammalian cells, including human cells, especially epithelial cells, cells of the immune system and cells of the central and peripheral nervous system. For example, in various cell types, EGF-induced activation of receptor-associated tyrosine protein kinase (EGF-R-TPK) is a prerequisite for cell division and hence for the proliferation of the cell population. An increase in the number of EGF-receptor-specific tyrosine kinase inhibitors thus inhibits the proliferation of the cells. The same applies analogously to the other protein kinases mentioned hereinbefore and hereinafter.

In addition to or instead of inhibiting EGF-receptor tyrosine protein kinase, the compounds of formula I also inhibit to varying extents other tyrosine protein kinases that are involved in signal transmission mediated by trophic factors, for example abl kinase, especially v-abl kinase, kinases from the family of the src kinases, especially c-src kinase, lck, fyn; other kinases of the EGF family, for example c-erbB2 kinase e (HER-2), c-erbB3 kinase, c-erbB4 kinase; members of the family of the PDGF-receptor tyrosine protein kinases, for example PDGF-receptor kinase, CSF-1 receptor kinase, Kit-receptor kinase, VEGF-receptor kinase (e.g. KDR and Flt-1) and FGF-receptor kinase; the receptor kinase of the insulin-like growth factor (IGF-1 kinase), and serine/threonine kinases, for example protein kinase C or cdc kinases, all of which play a part in growth regulation and transformation in mammalian cells, including human cells.

The inhibition of EGF-receptor-specific tyrosine protein kinase (EGF-R-TPK) can be demonstrated using known methods, for example using the recombinant intracellular domain of the EGF-receptor (EGF-R ICD; see, for example, E. McGlynn et al., Europ. J. Biochem. 207, 265–275 (1992)). Compared with the control without inhibitor, the compounds of formula I inhibit the enzyme activity by 50% ($IC_{50}$), for example in a concentration of from 0.0005 to 1 $\mu$M, especially from 0.001 to 0.1 $\mu$M.

The action of the compounds of formula I on EGF-stimulated cellular tyrosine phosphorylation in the EGF-receptor can be determined in the human A431 epithelial carcinoma cell line by means of an ELISA which is described in U. Trinks et al., J. Med. Chem. 37:7, 1015–1027 (1994). In that test (EGFR-ELISA) the compounds of formula I exhibit an $IC_{50}$ of approximately from 0.001 to 1 $\mu$M.

Stimulation of quiescent BALB/c3T3 cells with EGF rapidly induces the expression of c-fos mRNA. Pretreatment of the cells with a compound of formula I before the stimulation with EGF inhibits c-fos expression at an $IC_{50}$ of approximately from 0.001 to 0.1 $\mu$M. That test procedure is likewise described in U. Trinks et al., J. Med. Chem. 37:7,1015–1027 (1994).

In the micromolar range too, the compounds of formula I exhibit, for example, inhibition of the cell growth of EGF-dependent cell lines, for example the epidermoid BALB/c mouse keratinocyte cell line (see Weissmann, B. A., and Aaronson, S. A., Cell 32, 599 (1983)) or the A431 cell line, which are recognized useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory activity of the compounds of formula I is determined, briefly, as follows: BALB/MK cells (10 000/microtiter plate well) are transferred to 96-well microtiter plates. The test compounds (dissolved in DMSO) are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the MK cells is measured by means of methylene blue staining: after the incubation the cells are fixed with glutaraldehyde, washed with water and stained with 0.05% methylene blue. After a washing step the stain is eluted with 3% HCl and the optical density per well of the microtitre plate is measured using a Titertek Multiskan at 665 nm. $IC_{50}$ values are determined by a computer-aided system using the formula:

$$IC_{50}=[(OD_{test}-OD_{start})/(OD_{control}-OD_{start})] \times 100.$$

The $IC_{50}$ value in those experiments is given as that concentration of the test compound in question that results in a cell count that is 50% lower than that obtained using the control without inhibitor. The compounds of formula I exhibit inhibitory activity in the micromolar range, for example an $IC_{50}$ of approximately from 0.1 to 1 $\mu$M.

The compounds of formula I exhibit inhibition of the growth of tumor cells also in vivo, as shown, for example, by the test described below: the test is based on inhibition of the growth of the human epidermoid carcinoma A431 (ATCC No. CRL 1555; American Type Culture Collection, Rockville, Md., USA; see Santon, J. B., et al., Cancer Research 46, 4701–4705 (1986) and Ozawa, S., et al., Int. J. Cancer 40, 706–710 (1987)), which is transplanted into female BALB/c nude mice (Bomholtgard, Denmark). That carcinoma exhibits a growth that correlates with the extent of the expression of the EGF-receptor. In the experiment, tumors having a volume of approximately 1 cm³ cultured in vivo are surgically removed from experimental animals under sterile conditions. The tumors are comminuted and suspended in 10 volumes (w/v) of phosphate-buffered saline. The suspension is injected s.c. (0.2 ml/mouse in phosphate-buffered saline) into the left flank of the animals. Alternatively, $1 \times 10^6$ cells from an in vitro culture in 0.2 ml of phosphate-buffered saline can be injected. Treatment with test compounds of formula I is started 5 or 7 days after the transplant, when the tumors have reached a diameter of 4–5 mm. The test compound in question is administered (in different doses for different animal groups) once a day for 15 successive days. The tumor growth is determined by measuring the diameter of the tumors along three axes that are perpendicular to each other. The tumor volumes are calculated using the known formula $p \times L \times D^2/6$ (see Evans, B. D., et al., Brit. J. Cancer 45, 466–8 (1982)). The results are given as treatment/control percentages (T/C×100=T/C %). At a dose of from 3 to 50 mg/kg of active ingredient, distinct inhibition of the tumor growth is found, for example T/C % values of less than 10, which indicates strong inhibition of tumor growth.

As well as or instead of inhibiting EGF-receptor tyrosine protein kinase, the compounds of formula I also inhibit other tyrosine protein kinases that are involved in signal transmission mediated by trophic factors, for example abl kinase, such as especially v-abl kinase ($IC_{50}$ for example from 0.01 to 5 $\mu$M), kinases from the family of the src kinases, such as especially c-src kinase ($IC_{50}$ for example from 0.1 to 10 $\mu$M) and c-erbB2 kinase (HER-2), and serine/threonine kinases, for example protein kinase C, all of which are involved in growth regulation and transformation in mammalian cells, including human cells.

The above-mentioned inhibition of v-abl tyrosine kinase is determined by the methods of N. Lydon et al., Oncogene Research 5, 161–173 (1990) and J. F. Geissler et al., Cancer Research 52, 4492–4498 (1992). In those methods [Val⁵]-angiotensin II and [γ-³²P]-ATP are used as substrates.

The inhibition of c-erbB2 tyrosine kinase (HER-2) can be determined, for example, analogously to the method used for EGF-R-TPK (see C. House et al, Europ. J. Biochem. 140, 363–367 (1984)). The c-erbB2 kinase can be isolated, and its activity determined, by means of protocols known per se, for example in accordance with T. Akiyama et a., Science 232, 1644 (1986).

The compounds of formula I which inhibit the tyrosine kinase activity of the receptor for the epidermal growth factor (EGF) or of the other tyrosine protein kinases mentioned are therefore useful, for example, in the treatment of benign or malignant tumors. They are capable of effecting tumor regression and of preventing the formation of tumor metastases and the growth of micrometastases. They can be used especially in the case of epidermal hyperproliferation (psoriasis), in the treatment of neoplasias of epithelial character, e.g. mammary carcinomas, and in leukemias. In addition, the compounds of formula I (especially the novel compounds) can be used in the treatment of those disorders of the immune system in which several or, especially, individual tyrosine protein kinases and/or (furthermore) serine/threonine protetin kinases are involved; those compounds of formula I can also be used in the treatment of those disorders of the central or peripheral nervous system in which signal transmission by several or, especially, a single tyrosine protein kinase(s) and/or (furthermore) serine/threonine protein kinase(s) is/are involved.

In general, the present invention relates also to the use of the compounds of formula I in the inhibition of the mentioned protein kinases.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antiestrogens and/or cytostatic drugs.

In the preferred subjects of the invention mentioned hereinafter, general definitions can be replaced by the more specific definitions given at the beginning, where appropriate and expedient.

Preference is given to compounds of formula I wherein
q is 0 or 1,
n is from 1 to 3 when q is 0, or n is from 0 to 3 when q is 1,
R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different,
a) $R_1$ and $R_2$ are each independently of the other phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkyl-amino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a), or c) $R_1$ and $R_2$ together are $C_4$–$C_{10}$-1,4-alkadienylene substituted by amino, lower alkanoylamino, lower alkylamino, N,N-di-lower alkylamino, nitro, halogen, hydroxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, or d) when q is 1, $R_1$ and $R_2$ are each independently of the other unsubstituted lower alkyl or unsubstituted phenyl or have one of the meanings given above in paragraph a), and $R_6$ is hydrogen, lower alkyl, lower alkoxycarbonyl, carbamoyl, N-lower alkyl-carbamoyl or N,N-di-lower alkyl-carbamoyl, and to the salts thereof, with the exception of the compound of formula I wherein n is 0, q is 1, $R_1$ and $R_6$ are each hydrogen and $R_2$ is methyl.

Preference is given also to compounds of formula I wherein q is 0 or 1, n is from 1 to 3 when q is 0, or n is from 0 to 3 when q is 1, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ is hydrogen and $R_2$ is phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen; phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alky-lamino or by trifluoromethyl; lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are $C_4$–$C_{10}$-1,4-alkadienylene substituted by lower alkanoyl-amino, nitro, halogen, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, or d) when q is 1, $R_1$ is hydrogen and $R_2$ is unsubstituted phenyl, and $R_6$ is hydrogen, lower alkyl, lower alkoxycarbonyl, carbamoyl, N-lower alkyl-carbamoyl or N,N-di-lower alkyl-carbamoyl, and to the salts thereof.

Preference is given also to 7H-pyrrolo[2,3-d]pyrimidine derivatives of formula Ia

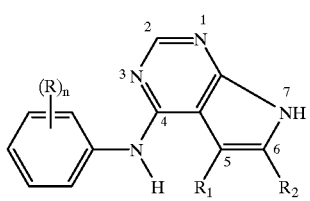

(Ia)

wherein n is from 1 to 3,

R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are $C_4$–$C_{10}$-1,4-alkadienylene substituted by amino, lower alkanoylamino, lower alkylamino, N,N-di-lower alkylamino, nitro, halogen, hydroxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, and to the salts thereof.

Preference is given very especially to compounds of formula I wherein n is from 1 to 3 and q is 0, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, and a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; unsubstituted or halo- or lower alkyl-substituted pyridyl; N-benzyl-pyridinium-2-yl; naphthyl; cyano; carboxy; lower alkoxy-carbonyl; carbamoyl; N-lower alkyl-carbamoyl; N,N-di-lower alkyl-carbamoyl; ormyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3—S(O)_m—$ wherein $R_3$ is lower alkyl and m is 0, 1 or 2, or b) one of the radicals $R_1$ and $R_2$ is hydrogen, unsubstituted lower alkyl or unsubstituted phenyl and the other of the radicals $R_1$ and $R_2$ has one of the meanings given above in paragraph a), or c) $R_1$ and $R_2$ together are $C_4–C_{10}$-1,4-alkadienylene substituted by amino, lower alkanoylamino, lower alkylamino, N,N-di-lower alkylamino, nitro, halogen, hydroxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, and to the salts thereof.

Preference is given especially to compounds of formula I wherein n is 1 or 2 and q is 0, R is halogen, it being possible when several radicals R are present in the molecule for those radicals to be identical or different, and a) $R_1$ and $R_2$ are each independently of the other phenyl substituted by phenyl, amino, hydroxy or by nitro; hydrogen; pyridyl; N-benzyl-pyridinium-2-yl; naphthyl; or lower alkyl substituted by di-lower alkylamino, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are aza-1,4-alkadienylene having up to 9 carbon atoms, and to the salts thereof.

Special preference is given to compounds of formula I wherein n is 1 or 2 and q is 0, R is halogen, it being possible when several radicals R are present in the molecule for those radicals to be identical or different, and a) $R_1$ is hydrogen, or lower alkyl unsubstituted or substituted by di-lower alkylamino, and $R_2$ is phenyl substituted by phenyl, amino, hydroxy or by nitro; pyridyl; N-benzylpyridinium-2-yl; or naphthyl, or b) $R_1$ and $R_2$ together are aza-1,4-alkadienylene having up to 9 carbon atoms, and to the salts thereof.

Preference is given also to compounds of formula I wherein q is 1, n is from 0 to 3, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3—S(O)_m—$ wherein $R_3$ is lower alkyl and m is 0,1 or 2, or b) $R_1$ and $R_2$ together are $C_4–C_{10}$-1,4-alkadienylene substituted by amino, lower alkanoylamino, lower alkylamino, N,N-di-lower alkylamino, nitro, halogen, hydroxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, or c) $R_1$ and $R_2$ are each independently of the other unsubstituted lower alkyl or unsubstituted phenyl or have one of the meanings given above in paragraph a), and $R_6$ is hydrogen, lower alkyl, lower alkoxycarbonyl, carbamoyl, N-lower alkyl-carbamoyl or N,N-di-lower alkyl-carbamoyl, and to the salts thereof.

Preference is given especially also to compounds of formula I wherein q is 0 or 1, n is 1 or 2 when q is 0, or n is from 0 to 2 when q is 1, R is halogen or lower alkyl, it being possible when several radicals R are present in the molecule for those radicals to be identical or different, and a) $R_1$ is hydrogen, or lower alkyl that is unsubstituted or substituted by di-lower alkylamino, and $R_2$ is phenyl substituted by carbamoylmethoxy, carboxymethoxy, benzyloxycarbonylmethoxy, lower alkoxycarbonylmethoxy, lower alkoxycarbonyl, carboxy, N,N-di-lower alkyl-carbamoyl, phenyl, amino, lower alkylamino, di-lower alkylamino, lower alkanoylamino, hydroxy or by nitro; hydroxy-lower alkyl, amino-lower alkyl, di-lower alkylamino-lower alkyl, piperazino-lower alkyl, formyl, cyano, carboxy; lower alkoxycarbonyl; carbamoyl, N-lower alkyl-carbamoyl; N,N-di-lower alkyl-carbamoyl, pyridyl; N-benzyl-carbamoyl, N-benzyl-pyridinium-2-yl; or naphthyl, or b) $R_1$ and $R_2$ together are 1-aza-buta-1,3-dien-1,4-ylene, or c) when q is 1, $R_1$ and $R_2$ are each methyl, and $R_6$ is hydrogen, methyl or lower alkoxycarbonyl, and to the salts thereof.

Preference is given especially also to compounds of formula I wherein q is 0 or 1, n is 1 or 2 when q is 0, or n is from 0 to 2 when q is 1,
R is halogen, it being possible when several radicals R are present in the molecule for those radicals to be identical or different, and a) $R_1$ is hydrogen or lower alkyl that is unsubstituted or substituted by di-lower alkylamino, and $R_2$ is phenyl substituted by carbamoylmethoxy, carboxymethoxy, benzyloxycarbonylmethoxy, methoxycarbonylmethoxy, ethoxycarbonyl, carboxy, phenyl, amino, acetamino, hydroxy or by nitro; carboxy; ethoxycarbonyl; N-lower alkyl-carbamoyl; pyridyl; N-benzyl-pyridinium-2-yl; or naphthyl, or b) $R_1$ and $R_2$ together are aza-1,4-alkadienylene having up to 9 carbon atoms, or c) when q is 1, $R_1$ and $R_2$ are each methyl, and $R_6$ is hydrogen, methyl or methoxycarbonyl, and to the salts thereof.

Preference is given above all to the compounds of formula I described in the Examples and to the pharmaceutically acceptable salts thereof.

The invention relates also to the compound 4-(3-chloro-anilino)-pyrimido[4,5-b]indole, which does not fall within the scope of formula I, which is obtainable in accordance with Example (Reference Example) 15, and to the pharmaceutically acceptable salts thereof.

The compounds of formula I and the salts thereof are prepared by processes known per se. The process according to the invention comprises a) reacting a pyrrolo[2,3-d]pyrimidine derivative of formula II

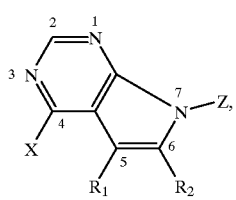

(II)

wherein X is a suitable leaving group, Z is hydrogen or 1-aryl-lower alkyl and the remaining substituents are as defined above for compounds of formula I, any free functional groups present in the radicals $R_1$ and $R_2$ being protected if necessary by readily removable protecting groups, with an amine of formula III

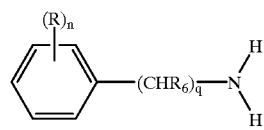

(III)

wherein R, $R_6$, n and q are as defined above for compounds of formula I, any free functional groups present in the radical R being protected if necessary by readily removable protecting groups, and removing any protecting groups that are present and, where it is present, the 1-aryl-lower alkyl radical Z, or b) reacting with an amine of formula III above, in the presence of a dehydrating agent and a tertiary amine, a pyrrolo[2,3-d]pyrimidin-4-one derivative of formula IV

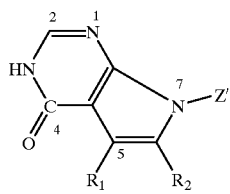

(IV)

wherein Z' is 1-aryl-lower alkyl and $R_1$ and $R_2$ are as defined above for compounds of formula I, any free functional groups present in the radicals $R_1$ and $R_2$ being protected if necessary by readily removable protecting groups, and removing any protecting groups that are present, or c) for the preparation of a compound of formula I wherein $R_1$ is dimethylamino-methyl and the remaining substituents are as defined above for compounds of formula I, reacting with N,N-dimethyl-methyleneimmonium iodide a compound corresponding to formula I wherein $R_1$ is hydrogen and the remaining substituents are as defined above for compounds of formula I, any free functional groups present in the radicals $R_1$ and $R_2$ being protected if necessary by readily removable protecting groups, and removing any protecting groups that are present, or d) for the preparation of a compound of formula I wherein at least one of the radicals R, $R_1$ and $R_2$ is hydroxy-substituted phenyl and the remaining substituents are as defined above for compounds of formula I, reacting with boron tribromide a compound corresponding to formula I wherein at least one of the radicals R, $R_1$ and $R_2$ is methoxy-substituted phenyl and the remaining substituents are as defined above for compounds of formula I, any free functional groups present in the radicals R, $R_1$ and $R_2$ being protected if necessary by readily removable protecting groups, and removing any protecting groups that are present, or e) for the preparation of a compound of formula I wherein at least one of the radicals R, $R_1$ and $R_2$ is amino-substituted phenyl and the remaining substituents are as defined above for compounds of formula I, subjecting to catalytic hydrogenation a compound corresponding to formula I wherein at least one of the radicals R, $R_1$ and $R_2$ is nitro-substituted phenyl and the remaining substituents are as defined above for compounds of formula I, any free functional groups present in the radicals R, $R_1$ and $R_2$ being protected if necessary by readily removable protecting groups, and removing any protecting groups that are present, and after carrying out one of process variants a) to e), if necessary for the preparation of a salt, converting a resulting free compound of formula I into a salt or, if necessary for the preparation of a free compound, converting a resulting salt of a compound of formula I into the free compound.

Detailed description of the process steps

The above processes are described in detail below (see also German Offenlegungsschrift No. 30 36 390, published on May 13, 1982, and A. Jorgensen et al., J. Heterocycl. Chem. 22, 859 [1985]). In the more precise description that follows, unless otherwise indicated the radicals R, $R_1$ and $R_2$ and n are as defined for compounds of formula 1.

General points:

The end products of formula I may contain substituents that can also be used as protecting groups in starting materials for the preparation of other end products of formula 1. Unless the context indicates otherwise, the term "protecting group" is used in this text to denote only a readily removable group that is not a constituent of the particular desired end product of formula I.

Process a)

In the compound of formula II a suitable leaving group X is preferably halogen, such as bromine, iodine or especially chlorine. 1-Aryl-lower alkyl Z is preferably 1-phenyl-lower alkyl, such as especially 1-phenylethyl or, more especially, benzyl.

Free functional groups present in the radicals $R_1$ and $R_2$, which are if necessary protected by readily removable protecting groups, are especially amino or lower alkylamino.

Protecting groups and their introduction and removal are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. It is a characteristic of protecting groups that they can be removed readily, i.e. without undesired secondary reactions taking place, for example by solvolysis, reduction, photolysis or also under physiological conditions.

A protected amino group may be present, for example, in the form of a readily cleavable acylamino, arylmethylamino, etherified mercaptoamino or 2-acyl-lower alk-1-enyl-amino group.

In such an acylamino group, acyl is, for example, the acyl radical of an organic carboxylic acid having, for example, up to 18 carbon atoms, especially an unsubstituted or substituted, for example halo- or aryl-substituted, alkanecarboxylic acid or an unsubstituted or substituted, for example halo-, lower alkoxy- or nitro-substituted, benzoic acid, or of a carbonic acid semiester. Such acyl groups are, for example, lower alkanoyl, such as formyl, acetyl or propionyl, halolower alkanoyl, such as 2-haloacetyl, especially 2-chloro-, 2-bromo-, 2-iodo-, 2,2,2-tri-fluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals which are preferably phenyl that is unsubstituted or mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxy carbonyl, for example 2,2,2-trichloroethoxycarbonyl, 2-bromoethoxycarbonyl or 2-iodoethoxycarbonyl, or 2-(trisubstituted silyl)-ethoxycarbonyl wherein the substituents are each independently of the others an unsubstituted or substituted, for example lower alkyl-, lower alkoxy-, aryl-, halo- or nitro-substituted, aliphatic, araliphatic, cycloaliphatic or aromatic hydrocarbon radical having up to 15 carbon atoms, such as corresponding, unsubstituted or substituted lower alkyl, phenyl-lower alkyl, cycloalkyl or phenyl, for example 2-tri-lower alkylsilyl-ethoxycarbonyl, such as 2-trimethylsilylethoxycarbonyl or 2-(di-n-butylmethyl-silyl)-ethoxycarbonyl, or 2-triarylsilylethoxycarbonyl, such as 2-triphenylsilylethoxycarbonyl.

In an arylmethylamino group, which is a mono-, di- or especially tri-arylmethyl-amino group, the aryl radicals are especially unsubstituted or substituted phenyl radicals. Such groups are, for example, benzyl-, diphenylmethyl- and especially trityl-amino.

An etherified mercapto group in an amino group protected by such a radical is especially arylthio or aryl-lower alkylthio, wherein aryl is, especially, phenyl that is unsubstituted or substituted, for example, by lower alkyl, such as methyl or tert-butyl, lower alkoxy, such as methoxy, halogen, such as chlorine, and/or by nitro.

A corresponding amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, such as 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butyloxycarbonyl, benzyloxycarbonyl that is unsubstituted or substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, also trityl or formyl.

The reaction between the derivative of formula II and the amine of formula III takes place in suitable inert polar solvents, especially alcohols, for example lower alkanols, such as methanol, propanol, isopropanol or especially ethanol or n-butanol. In some cases, the addition of a solubilizer, such as 1,3-dimethyl-3,4,5,6-tetrahydro-2(1H)-pyrimidinone (DMPU), is advantageous. The reaction takes place at elevated temperatures, for example in a temperature range of from 70 to 150° C., preferably under reflux conditions.

If Z in the compound of formula II is 1-aryl-lower alkyl, that radical is removed from the resulting precursor of the compound of formula I (with Z instead of the hydrogen atom at the nitrogen). That is effected, for example, by treatment with protonic acids, such as hydrochloric acid, phosphoric acids or polyphosphoric acid, at preferred temperatures of from 20° C. to 150° C. and where appropriate in the presence of water (that is especially the preferred method for Z=1-phenylethyl); or preferably by treatment with Lewis acids, especially $AlCl_3$, in an aromatic solvent, especially in benzene and/or toluene, at elevated temperature, especially under reflux [that is especially the preferred variant for Z=benzyl; see also the analogous process in Chem. Pharm. Bull. 39(5), 1152 (1991)].

The removal of the protecting groups that are not constituents of the desired end product of formula I is effected in a manner known per se, for example by means of solvolysis, especially hydrolysis, alcoholysis or acidolysis, or by means of reduction, especially hydrogenolysis or chemical reduction, where appropriate step-wise or simultaneously.

A protected amino group is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-trisubstituted silylethoxycarbonylamino can be cleaved by treatment with a suitable acid, for example formic acid or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and subsequent solvolysis, such as alcoholysis or hydrolysis, of the resulting condensation product. An amino group protected by 2-substituted silylethoxycarbonyl can be converted into the free amino group also by treatment with a salt of hydrofluoric acid that yields fluoride anions.

Process b)

1-Aryl-lower alkyl Z' in a compound of formula IV is especially 1-phenylethyl and also benzyl.

The compound of formula IV is in tautomeric equilibrium (lactam/lactim form), the lactam form (formula IV) presumably predominating. Formula IV is used to represent the two possible equilibrium forms.

The lactim form has the formula IVa

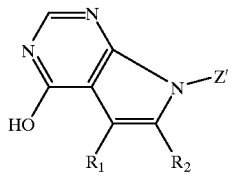

(IVa)

wherein the radicals are as defined for compounds of formula IV.

The present invention relates likewise to the novel compounds of formulae IV and IVa.

There is used as dehydrating agent especially a strong chemical dehydrating agent, especially phosphorus pentoxide ($P_4O_{10}$).

Suitable as tertiary amine is especially ammonia substituted by three radicals selected independently of one another from alkyl, especially lower alkyl, such as methyl or ethyl, and cycloalkyl having from 3 to 7 carbon atoms, especially cyclohexyl, for example N,N-dimethyl-N-cyclohexylamine, N-ethyl-N,N-diisopropylamine or triethylamine, or, furthermore, also pyridine, N-methylmorpholine or 4-dimethylaminopyridine.

The reaction between the pyrrolo-pyrimidinone of formula IV and the amine of formula III takes place at elevated temperature, for example at from 200 to 250° C.

Process c)

The reaction is carried out with the exclusion of moisture in a suitable inert solvent, for example a suitable ether, such as a cyclic ether, such as especially tetrahydrofuran, at elevated temperature, preferably under reflux.

Process d)

The reaction is carried out with the exclusion of moisture in a suitable inert solvent, for example a suitable halogenated hydrocarbon, such as especially methylene chloride, at temperatures of from approximately −20° C. to +50° C., preferably with ice-cooling or at room temperature.

Process e)

The hydrogenation is carried out under elevated pressure or preferably under normal pressure in the presence of a suitable hydrogenation catalyst, such as especially Raney nickel, in an inert solvent or solvent mixture, such as especially a mixture of a suitable cyclic ether and a suitable lower alkanol, such as preferably a mixture of tetrahydrofuran and methanol, at temperatures of approximately from 0° C. to +50° C., preferably at room temperature.

Starting materials:

The starting materials of formula II are novel and the present invention relates also thereto. They can be prepared by processes analogous to those described in German Offenlegungsschrift No. 28 18 676 (published Nov. 8, 1979) and German Offenlegungsschrift No. 30 36 390 (published on May 13, 1982).

The starting material of formula II wherein X is chlorine is obtained, for example, from a compound analogous to formula II wherein X is hydroxy by reaction with phosphorus oxychloride (phosphoryl chloride, $P(=O)Cl_3$) with the exclusion of moisture at the reflux temperature. If desired, the further reaction of the starting material of formula II thus obtained wherein X is chlorine can be carried out with an amine of formula III in the same vessel, i.e. as a one-pot reaction. For that purpose, once the reaction with phosphorus oxychloride is complete, the reaction mixture from that reaction is concentrated to dryness by evaporation, made into a suspension with a suitable solvent, such as n-butanol, and reacted further with the amine of formula Ill.

A compound analogous to formula II wherein X is hydroxy is obtained, for example, from a compound of formula V

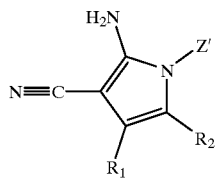

(V)

wherein the substituents are as defined above, by reaction with formic acid which is preferably used in excess relative to the compound of formula V, for example in a 10 to 30 molar excess, where appropriate in the presence of inert solvents, such as dimethylformamide, at elevated temperature, for example at temperatures of from 80° C. to the boiling temperature. Alternatively, a compound analogous to formula II wherein X is hydroxy and the remaining symbols are as defined above is obtained, for example, from a compound of formula VI

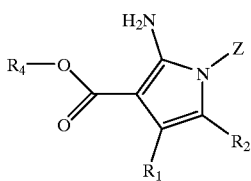

(VI)

wherein $R_4$ is lower alkyl, such as especially ethyl, and the remaining symbols are as defined above, by reaction with a large excess of formamide in a mixture of anhydrous dimethylformamide and formic acid. The reaction is carried out at elevated temperature, for example at from 100° C. to 150° C., and preferably under a protecting gas.

The present invention relates also to the novel starting materials of formulae V and VI.

The 1-(Z')-2-amino-3-cyano-pyrroles of formula V used as intermediates can be prepared in good yields by methods that are known per se and have been published [see, for example, Roth, H. J., and Eger, K., Arch. Pharmaz. 308, 179 (1975)]. For that purpose, for example, a compound of formula VII

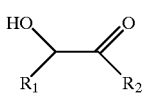

(VII)

is reacted first with an amine of the formula $Z'$-$NH_2$ to form a compound of formula VIII

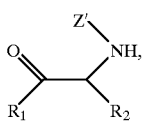

(VIII)

which is then converted with malonic acid dinitrile of the formula $CH_2(CN)_2$ into the desired intermediate of formula V. In detail, the reaction with the amine $Z'$-$NH_2$ is carried out under customary condensation conditions, for example in the presence of catalytic amounts of a strong acid, for example hydrochloric acid or p-toluenesulfonic acid, at elevated temperature (preferably at the boiling temperature) in a suitable solvent, for example benzene or toluene, with the removal of water, to form the respective α-amino ketone of formula VII. The latter is not isolated but is immediately condensed with malonic acid dinitrile with heating and with further removal of water, if necessary with the addition of a small amount of a base, such as piperidine, a compound of formula V being obtained.

The compounds of formula VI wherein $R_2$ is N-benzyl-pyridinium-2-yl and the remaining symbols are as defined above that are used as intermediates are obtained, for example, by reacting a compound of formula VI wherein $R_2$ is hydrogen and the remaining symbols are as defined above with N-benzyl-2-bromo-pyridinium bromide in a suitable solvent, such as a halogenated hydrocarbon, such as especially methylene chloride. The reaction is preferably carried out under a protective gas, in the dark and under anhydrous conditions at room temperature or elevated temperature, for example at from 20° C. to 80° C., and in the presence of 2,6-dimethyl-pyridine (2,6-lutidine). The remaining compounds of formula VI are obtained, for example, by reacting a 2-amidino-acetic acid lower alkyl ester of formula IX

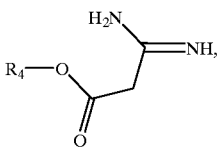

(IX)

wherein $R_4$ is as defined above, with a 2-X-1-$R_2$-ethan-1-one derivative of formula X

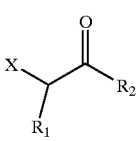

(X)

wherein the substituents are as defined above. The leaving group X is preferably bromine. The 2-amidino-acetic acid lower alkyl ester of formula IX is freed from its acid addition salt, such as especially its hydrochloride, before the start of the reaction with the aid of equinormal amounts of a base, such as especially sodium ethanolate, with ice-cooling. The reaction is carried out in a suitable solvent, such as especially a lower alkanol, such as preferably ethanol, at preferred temperatures of from 0° C. to 50° C., especially at room temperature.

General process conditions:

Free compounds of formula I having salt-forming properties that are obtainable according to the process can be converted into their salts in a manner known per se, for example by treatment with acids or suitable derivatives thereof, for example by the addition of the appropriate acid to the compound of formula I dissolved in a suitable solvent, for example an ether, such as a cyclic ether, especially dioxane or more especially tetrahydrofuran.

Mixtures of isomers obtainable according to the invention can be separated into the individual isomers in a manner known per se; racemates can be separated, for example, by forming salts with optically pure salt-forming reagents and separating the mixture of diastereoisomers thus obtainable, for example by means of fractional crystallization.

The reactions described above can be carried out under reaction conditions known per se, in the absence or, customarily, the presence of solvents or diluents, preferably those that are inert towards the reagents used and are solvents therefor, in the absence or presence of catalysts, condensation agents (for example phosphorus pentoxide) or neutralizing agents, for example bases, especially nitrogen bases, such as triethylamine hydrochloride, depending on the nature of the reaction and/or of the reactants at reduced, normal or elevated temperature, for example in a temperature range of from approximately −80° C. to approximately 200° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere.

The specific reaction conditions given in each case are preferred.

Solvents and diluents are, for example, water, alcohols, for example lower alkyl hydroxides, such as methanol, ethanol, propanol or especially butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, especially formic acid or acetic acid, amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bis-alkanesulfines, such as dimethyl sulfoxide, nitrogen-containing heterocyclic compounds, such as pyridine, hydrocarbons, for example lower alkanes, such as heptane, or aromatic compounds, such as benzene, toluene or xylene(s), or mixtures of those solvents, it being possible for the solvents suitable for the above-mentioned reactions to be selected in each case.

Customary processes are used for working up the obtainable compounds of formula I or the salts thereof, for example solvolysis of excess reagents; recrystallization; chromatography, for example partition, ion or gel chromatography; partitioning between inorganic and organic solvent phases; single or multiple extraction, especially after acidifying or increasing the basicity or the salt content; drying over hygroscopic salts; digesting; filtering; washing; dissolving; concentrating by evaporation (if necessary in vacuo or under a high vacuum); distillation; crystallization, for example of compounds obtained in oil form or from the mother liquor, inoculation with a crystal of the end product also being possible; or a combination of two or more of the mentioned working-up steps, which can also be used repeatedly, etc.

Starting materials and intermediates can be used in pure form, for example after working-up, as just mentioned, in partly purified form or also, for example, directly in the form of the crude product.

In view of the close relationship between the compounds of formula I in free form and in the form of salts, hereinabove and hereinbelow any reference to the free compounds and their salts is to be understood as including also the corresponding salts and free compounds, respectively, as appropriate and expedient, provided that the compounds contain salt-forming groups.

The compounds, including their salts, may also be obtained in the form of hydrates, or their crystals may include, for example, the solvent used for crystallization.

In the process of the present invention, the starting materials used are preferably those that lead to the novel compounds of formula I described at the beginning as being especially valuable.

The invention relates also to those forms of the process according to which a compound obtainable as intermediate at any stage of the process is used as starting material and the remaining process steps are carried out or in which a starting material is formed under the reaction conditions or is used in the form of a derivative, for example a salt, thereof.

The invention relates especially to a process for the preparation of a 7H-pyrrolo[2,3-d]-pyrimidine derivative of formula Ia, which falls within the scope of formula I

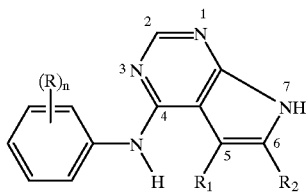

and wherein
n is from 1 to 3,
R is hydrogen, halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, and
a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or
b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or
c) $R_1$ and $R_2$ together are $C_4$–$C_{10}$-1,4-alkadienylene that is unsubstituted or substituted by amino, lower alkanoylamino, lower alkylamino, N,N-di-lower alkylamino, nitro, halogen, hydroxy, lower alkoxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, or a salt thereof,
which comprises
a) reacting a pyrrolo[2,3-d]pyrimidine derivative of formula II

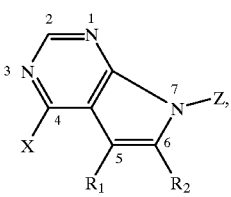

wherein X is a suitable leaving group, Z is hydrogen or 1-aryl-lower alkyl and the remaining substituents are as defined above for compounds of formula Ia, any free functional groups present in the radicals $R_1$ and $R_2$ being protected if necessary by readily removable protecting groups, with an aniline derivative of formula IIIa

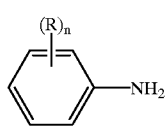

(IIIa)

wherein R and n are as defined above for compounds of formula Ia, any free functional groups present in the radical R being protected if necessary by readily removable protecting groups, and removing any protecting groups that are present and, where it is present, the 1-aryl-lower alkyl radical Z, or b) reacting with a phenylamine of formula IIIa above, in the presence of a dehydrating agent and a tertiary amine, a pyrrolo[2,3-d]pyrimidin-4-one derivative of formula IV

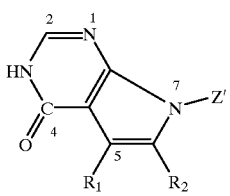

(IV)

wherein Z' is 1-aryl-lower alkyl and $R_1$ and $R_2$ are as defined above for compounds of formula Ia, any free functional groups present in the radicals $R_1$ and $R_2$ being protected if necessary by readily removable protecting groups, and removing any protecting groups that are present, or c) for the preparation of a compound of formula Ia wherein $R_1$ is dimethylamino-methyl and the remaining substituents are as defined above for compounds of formula Ia, reacting with N,N-dimethyl-methyleneimmonium iodide a compound corresponding to formula Ia wherein $R_1$ is hydrogen and the remaining substituents are as defined above for compounds of formula Ia, any free functional groups present in the radicals $R_1$ and $R_2$ being protected if necessary by readily removable protecting groups, and removing any protecting groups that are present, or d) for the preparation of a compound of formula Ia wherein at least one of the radicals R, $R_1$ and $R_2$ is hydroxy-substituted phenyl and the remaining substituents are as defined above for compounds of formula Ia, reacting with boron tribromide a compound corresponding to formula Ia wherein at least one of the radicals R, $R_1$ and $R_2$ is methoxy-substituted phenyl and the remaining substituents are as defined above for compounds of formula Ia, any free functional groups present in the radicals R, $R_1$ and $R_2$ being protected if necessary by readily removable protecting groups, and removing any protecting groups that are present, or e) for the preparation of a compound of formula Ia wherein at least one of the radicals R, $R_1$ and $R_2$ is amino-substituted phenyl and the remaining substituents are as defined above for compounds of formula Ia, subjecting to catalytic hydrogenation a compound corresponding to formula Ia wherein at least one of the radicals R, $R_1$ and $R_2$ is nitro-substituted phenyl and the remaining substituents are as defined above for compounds of formula Ia, any free functional groups present in the radicals R, $R_1$ and $R_2$ being protected if necessary by readily removable protecting groups, and removing any protecting groups that are present, and after carrying out one of process variants a) to e), if necessary for the preparation of a salt, converting a resulting free compound of formula Ia into a salt or, if necessary for the preparation of a free compound, converting a resulting salt of a compound of formula Ia into the free compound.

The invention relates also to a pyrrolo[2,3-d]pyrimidine derivative of formula IIa

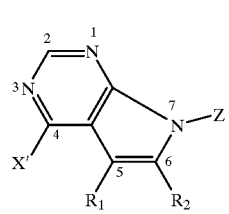

(IIa)

wherein X' is hydroxy or a suitable leaving group,
Z is hydrogen or 1-aryl-lower alkyl,
$R_1$ is hydrogen or lower alkyl that is unsubstituted or substituted by di-lower alkylamino, and $R_2$ is
a) phenyl substituted by carbamoylmethoxy, carboxymethoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro;
b) unsubstituted or halo- or lower alkyl-substituted pyridyl;
c) N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or
d) lower alkyl substituted by
α) halogen, amino, lower alkylamino, piperazino, di-lower alkylamino,
β) phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl,
γ) hydroxy, lower alkoxy, cyano, carboxy, lower alkoxycarbonyl, carbamoyl, N-lower alkyl-carbamoyl, N,N-di-lower alkyl-carbamoyl, mercapto or
δ) by a radical of the formula $R_3—S(O)_m—$ wherein $R_3$ is lower alkyl and m is 0, 1 or 2, a 4-keto derivative that is a tautomer of a compound of formula II wherein X' is hydroxy, or a salt of such a compound.

The invention relates also to pyrrolo[2,3-d]pyrimidine derivatives of formula IIa

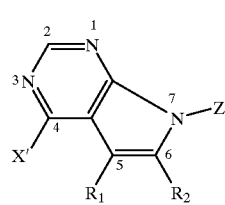

(IIa)

wherein X' is hydroxy or a leaving group,
Z is hydrogen or 1-aryl-lower alkyl, and a) $R_1$ and $R_2$ are each independently of the other phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen, amino, lower alkylamino, piperazino, di-lower alkylamino, phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are $C_4$–$C_{10}$-1,4-alkadienylene that is unsubstituted or substituted by amino, lower alkanoylamino, lower alkylamino, N,N-di-lower alkylamino, nitro, halogen, hydroxy, lower alkoxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, and to the 4-keto derivatives that are tautomers of the compounds of formula IIa wherein X' is hydroxy, and to salts of those compounds.

The invention relates especially to pyrrolo[2,3-d]pyrimidine derivatives of formula IIa wherein X' is hydroxy or a leaving group, Z is hydrogen or 1-aryl-lower alkyl, and a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are $C_4$–$C_{10}$-1,4-alkadienylene that is unsubstituted or substituted by amino, lower alkanoylamino, lower alkylamino, N,N-di-lower alkylamino, nitro, halogen, hydroxy, lower alkoxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, and to the 4-keto derivatives that are tautomers of the compounds of formula IIa wherein X' is hydroxy, and to salts of those compounds.

The compounds of formula IIa and the 4-keto derivatives that are tautomers of the compounds of formula IIa wherein X' is hydroxy can be used as starting materials of the formulae II, IV and IVa shown above and are prepared analogously to those starting materials.

The invention relates also to pyrrole derivatives of formula XI

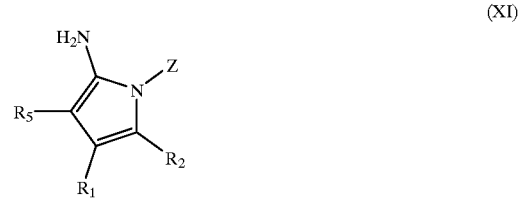

wherein Z is hydrogen or 1-aryl-lower alkyl, a) $R_1$ is hydrogen or lower alkyl that is unsubstituted or substituted by di-lower alkylamino, and $R_2$ is α) phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro;

β) unsubstituted or halo- or lower alkyl-substituted pyridyl;

γ) N-benzyl-pyridinium-2-yl; naphthyl; cyano; carboxy; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or δ) lower alkyl substituted by δα) halogen, amino, lower alkylamino, piperazino, di-lower alkylamino, δβ) phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl, δγ) hydroxy, lower alkoxy, cyano, carboxy, carbamoyl, N-lower alkyl-carbamoyl, N,N-di-lower alkyl-carbamoyl, or δδ) by a radical of the formula $R_3$—$S(O)_m$— wherein $R_3$ is lower alkyl and m is 0, 1 or 2, or b) $R_1$ and $R_2$ together are aza-1,4-alkadienylene having up to 9 carbon atoms, and $R_5$ is cyano or lower alkoxycarbonyl, and to salts of such compounds.

The invention relates especially to pyrrole derivatives of formula XI wherein Z is hydrogen or 1-aryl-lower alkyl, a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3-S(O)_m-$ wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) $R_1$ and $R_2$ together are $C_4-C_{10}$-1,4-alkadienylene that is unsubstituted or substituted by amino, lower alkanoylamino, lower alkylamino, N,N-di-lower alkylamino, nitro, halogen, hydroxy, lower alkoxy, lower alkanoyloxy, carboxy, lower alkoxycarbonyl, carbamoyl, N-lower alkyl-carbamoyl, N,N-di-lower alkyl-carbamoyl or by cyano, or are aza-1,4-alkadienylene having up to 9 carbon atoms, $R_5$ is cyano or lower alkoxycarbonyl, and to salts of those compounds.

The pyrrole derivatives of formula XI can be used as starting materials of formulae V and VI shown above and are prepared analogously to those starting materials.

The invention relates also to intermediates of formulae IIa and XI wherein the substituents are so defined that the compounds of formula I according to claim 1 are obtained. Pharmaceutical compositions, the preparation thereof and the use according to the invention of the compounds of formula I and of compositions comprising those compounds as active ingredient The present invention relates also to pharmaceutical compositions that comprise one of the compounds of formula I as active ingredient and that can be used especially in the treatment of the diseases mentioned above. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient on its own or, preferably, together with a pharmaceutically acceptable carrier. The dosage of the active ingredient depends upon the disease to be treated and upon the species, its age, weight and individual condition, the individual pharmacokinetic data, the disease to be treated and also upon the mode of administration.

The invention relates also to pharmaceutical compositions for use in a method for the therapeutic treatment of the human or animal body, to a process for the preparation thereof (especially in the form of compositions for the treatment of tumors) and to a method of treating tumor diseases, especially those mentioned above.

Preference is given to a pharmaceutical composition that is suitable for administration to a warm-blooded animal, especially a human, suffering from a disease that is responsive to the inhibition of a protein kinase, for example psoriasis or a tumor, comprising a compound of formula I, or a salt thereof when salt-forming groups are present, in an amount effective in the inhibition of protein kinase, together with at least one pharmaceutically acceptable carrier.

The pharmaceutical compositions comprise from approximately 1% to approximately 95% active ingredient, dosage forms in single dose form preferably comprising from approximately 20% to approximately 90% active ingredient and dosage forms that are not in single dose form preferably comprising from approximately 5% to approximately 20% active ingredient. Unit dose forms are, for example, dragées, tablets, ampoules, vials, suppositories or capsules. Other forms of administration are, for example, ointments, creams, pastes, foams, tinctures, lipsticks, drops, sprays, dispersions, etc. Examples are capsules, comprising from approximately 0.05 g to approximately 1.0 g of active ingredient.

The pharmaceutical compositions of the present invention are prepared in a manner known per se, for example by means of conventional mixing, granulating, confectioning, dissolving or lyophilizing processes.

Preference is given to the use of solutions of the active ingredient, and also suspensions or dispersions, especially isotonic aqueous solutions, dispersions or suspensions which, for example in the case of lyophilized compositions which comprise the active ingredient on its own or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating the osmotic pressure and/or buffers and are prepared in a manner known per se, for example by means of conventional dissolving and lyophilizing processes. The solutions or suspensions mentioned may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester, Gattefossé, France) and/or "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained, for example, by combining the active ingredient with one or more solid carriers, if desired granulating a resulting mixture, and processing the mixture or granules, if desired or necessary, by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticizer, such as glycerol or sorbitol. The dry-filled capsules may contain the active ingredient in the form of granules, for example in admixture with fillers, such as corn starch, binders and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution prior to parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

Ointments are oil-in-water emulsions that contain up to 70%, but preferably from 20% to 50%, water or aqueous phase. Suitable as fatty phase are especially hydrocarbons, for example petroleum jelly, paraffin oil or hard paraffins, which, in order to improve the water-binding capacity, preferably contain suitable hydroxy compounds, such as fatty alcohols or esters thereof, for example cetyl alcohol or wool wax alcohols, such as wool wax. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, and also preservatives and perfumes.

Fatty ointments are anhydrous and contain as base especially hydrocarbons, for example paraffin, petroleum jelly or paraffin oil, also natural or partially synthetic fats, for example coconut fatty acid triglyceride, or preferably hardened oils, for example hydrogenated groundnut oil or castor oil, also fatty acid partial esters of glycerol, for example glycerol mono- and/or di-stearate, and also, for example, the fatty alcohols increasing the water-absorption, emulsifiers and/or additives mentioned in connection with the ointments.

Creams are oil-in-water emulsions that contain more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens), and also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia, agents that reduce the drying out of the creams, for example polyalcohols, such as glycerol, sorbitol, propylene glycol and/or polyethylene glycols, and also preservatives and perfumes.

Pastes are creams and ointments having secretion-absorbing powder constituents, such as metal oxides, for example titanium oxide or zinc oxide, also talcum and/or aluminum silicates, the purpose of which is to bind any moisture or secretions present.

Foams are administered from pressurized containers and are liquid oil-in-water emulsions in aerosol form; halogenated hydrocarbons, such as chlorofluoro-lower alkanes, for example dichlorodifluoromethane and dichlorotetrafluoroethane, or preferably non-halogenated gaseous hydrocarbons, air, $N_2O$ or carbon dioxide, are used as propellant gases. As oil phase there are used, inter alia, those used above in the case of ointments and creams; the additives mentioned in that connection are also used.

Tinctures and solutions generally have an aqueous-ethanolic base to which there are added, inter alia, polyalcohols, for example glycerol, glycols and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other adjuncts and additives.

The invention relates also to a process or a method of treating the above-mentioned pathological conditions, especially those conditions responsive to the inhibition of protein kinases. The compounds of formula I can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a body weight of about 70 kg the daily dose administered is from approximately 0.1 g to approximately 5 g, preferably from approximately 0.5 g to approximately 2 g, of a compound of the present invention.

The following Examples serve to illustrate the invention without limiting the scope thereof.

The short forms and abbreviations used have the following definitions:

Eluants (gradients):

HPLC gradients:

Grad$_{20}$ 20% <100% a) in b) for 20 min.

Eluant a): acetonitrile +0.05% TFA; eluant b): water +0.05% TFA. Column (250 x 4.6 mm) filled with reversed-phase material C$_{18}$-Nucleosil® (5 pm average particle size, silica gel covalently derivatized with octadecylsilanes, Macherey & Nagel, Düren, Germany). Detection by UV absorption at 254 nm. The retention times (t$_{Ret}$) are given in minutes. Flow rate: 1 ml/min.

| Abbreviations | |
|---|---|
| abs. | absolute (anhydrous) |
| brine | saturated sodium chloride solution |
| DEPC | diethyl pyrocarbonate (dicarbonic acid diethyl ester) |
| DMF | dimethylformamide |
| DMPU | 1,3-dimethyl-3,4,5,6-tetrahydro-2(1H)-pyrimidinone |
| DMSO | dimethyl sulfoxide |
| EI-MS | electron impact ionization mass spectroscopy |
| FAB-MS | fast atom bombardment mass spectroscopy |
| HPLC | high-pressure liquid chromatography |
| HV | high vacuum |
| min | minute(s) |
| m.p. | melting point |
| MS | mass spectroscopy |
| RT | room temperature |
| TFA | trifluoroacetic acid |
| THF | tetrahydrofuran |
| TLC | thin-layer chromatogram |
| TLC-R$_f$ | R$_f$ value according to thin-layer chromatography |
| TPTU | O-(1,2-dihydro-2-oxo-1-pyridyl)-N,N,N',N'-tetramethyl-uronium tetrafluoroborate |

| Abbreviations used in data for NMR spectra | |
|---|---|
| b | broad |
| d | doublet |
| J | coupling constant |
| m | multiplet |
| q | quartet |
| s | singlet |
| t | triplet |

Remarks:

"Hexane" on its own denotes a mixture of the hexane isomers. "Butanol" on its own denotes "n-butanol".

EXAMPLE 1

4-(3-Chloro-anilino)-6-(pyrid-2-yl)-7H-pyrrolo[2,3-d] pyrimidine

Under an argon atmosphere, 40 ml of DMPU are added to 6.53 g (28.3 mmol) of 4-chloro-6-(pyrid-2-yl)-7H-pyrrolo [2,3-d]pyrimidine and 4.46 ml (42.5 mmol) of 3-chloro-aniline in 90 ml of n-butanol and the reaction mixture is stirred at 140° C. for 12 hours. The dark-brown suspension is cooled and filtered. Further product can be obtained from the mother liquor by precipitation with 100 ml of water. Digestion with ethanol/THF yields the title compound; m.p.>300° C.; $^1$H-NMR (360 MHz, DMSO-d$_6$): 12.49 and 9.66 (2s, 2H), 8.63 (d, J=5, 1H), 8.40 and 8.25 (2s, 2H), 7.91 (m, 2H), 7.84 (d, J=8, 1H), 7.57 (s, 1H), 7.33 (m, 2H), 7.06 (d, J=8, 1H); HPLC: t$_{Ret}$(Grad$_{20}$)=10.1 min; MS: (M)$^+$=321.

The starting material is prepared as follows:

Step 1.1: 2-(5-Amino-4-ethoxycarbonyl-1H-pyrrol-2-yl)-N-benzyl-pyridinium bromide Under an argon atmosphere, 658 mg (2.0 mmol) of N-benzyl-2-bromo-pyridinium bromide (for preparation see: J. Heterocyclic Chem. 28, 1083 (1991)) are introduced into 20 ml of abs. methylene chloride, and 308 mg (2.0 mmol) of 2-amino-pyrrole-3-carboxylic acid ethyl ester [for preparation see: J. Heterocyclic Chem. 23, 1555 (1986)] are added thereto. The reaction mixture is stirred for 2 days with the exclusion of light. Since the reaction is not complete, 232 µl (2 mmol) of 2,6-lutidine and a further 0.20 mmol of 2-amino-pyrrole-3-carboxylic acid ethyl ester are added. After a further 12 hours' stirring, the reaction mixture is concentrated by evaporation and the residue is digested in isopropanol. Filtering, washing with hexane and drying yield the title compound which, according to its $^1$H-NMR spectrum, still contains approximately 10% N-benzyl-2-bromo-pyridinium bromide; $^1$H-NMR (300 MHz, DMSO-d$_6$): 11.45 (1H), 8.70 (d, J=7, 1H), 8.38 (t, J=7, 1H), 8.00 (d, J=7, 1H), 7.67 (t, J=7, 1H), 7.42 (m, 3H), 7.14 (d, J=7, 2H), 6.85 (d, J=3, 1H), 6.45 (sb, 2H), 5.91 (s, 2H), 4.13 (q, J=7, 2H), 1.19 (t, J=7, 3H); FAB-MS: (M+H)$^+$=322.

Step 1.2: 6-(Pyrid-2-yl)-7H-pyrrolo[2,3-d]pyrimidin-4-ol

Under a protective gas, 27.07 g of 2-(5-amino-4-ethoxycarbonyl-1H-pyrrol-2-yl)-N-benzyl-pyridinium bromide in 195 ml of formamide are heated for 16 hours at 150° C. with 97.6 ml of DMF (dried over 4A molecular sieve) and 48.8 ml of formic acid. When the dark-brown reaction mixture is cooled in an ice-bath, the title compound crystallizes and can be filtered off and washed with isopropanol and diethyl ether; $^1$H-NMR (300 MHz, DMSO-d$_6$): 12.5 and 11.9 (2s, 2H), 8.60 (d, J=7, 1H), 8.05–7.8 (m, 3H), 7.28 (dd, J$_1$=7, J$_2$=9, 1H), 7.20 (s, 1H); FAB-MS: (M+H)$^+$=213.

Step 1.3: 4-Chloro-6-(pyrid-2-yl)-7H-pyrrolo[2,3-d] pyrimidine With the exclusion of moisture, 7.05 g (33.2 mmol) of 6-(pyrid-2-yl)-7H-pyrrolo[2,3-d]-pyrimidin-4-ol and 70 ml of phosphorus oxychloride are heated at boiling for 2 hours. The dark-brown suspension is concentrated by evaporation to a residual volume of 20 ml. The residue is introduced in portions into water, neutralized with solid NaHCO$_3$ and 0.2 liter of ethyl acetate is added thereto. Filtering and washing with hot THF yield the title compound; $^1$H-NMR (300 MHz, DMSO-d$_6$): 13.2 (sb, 1H), 8.72 (d, J=7, 1H), 8.63 (s, 1H), 8.23 (d, J=11, 1H), 7.97 (t, J=11, 1H), 7.46 (dd, J$_1$=7, J$_2$=11, 1H), 7.35 (s, 1H). Further product can be isolated from the filtrate and the THF washing solution, which is concentrated by evaporation, by partitioning between ethyl acetate/water and digesting in ethyl acetate/diethyl ether.

EXAMPLE 2

4-(3-Chloro-anilino)-6-(pyrid-2-yl)-7H-pyrrolo[2,3-d] pyrimidine hydrochloride 1.48 g (4.6 mmol) of 4-(3-chloro-anilino)-6-(pyrid-2-yl)-7H-pyrrolo[2,3-d]pyrimidine (see Example 1) are suspended in 115 ml of dioxane; with cooling, 46 ml of 0.1 N HCl solution (0.1 normal hydrochloric acid solution) are added and the reaction suspension is stirred at RT for 2.5 hours. The suspension is concentrated by evaporation and the residue is stirred in 400 ml of hot methanol and filtered. The filtrate is filtered while hot through activated carbon, concentrated by evaporation and digested in cold ethanol; m.p. 276–278° C.; $^1$H-NMR (200 MHz, DMSO-d$_6$): 13.1 and 10.7 (2s, 2H), 8.71 (d, J=5, 1H), 8.45 and 8.08 (2s, 2H), 8.00 (m, 2H), 7.76 (d, J=8, 1H), 7.68 (s, 1H), 7.50 (d, J=8, 1H), 7.42 (m, 1H), 7.27 (d, J=8, 1H).

EXAMPLE 3

4-(3-Chloro-anilino)-5-dimethylaminomethyl-6-(pyrid-2-yl)-7H-pyrrolo-[2,3-d]pyrimidine With the exclusion of moisture, 60.1 mg (0.325 mmol) of N,N-dimethyl-methylene-immonium iodide (Fluka; Buchs/Switzerland) are added to 80.4 mg (0.25 mmol) of 4-(3-chloro-anilino)-6-(pyrid-2-yl)-7H-pyrrolo[2,3-d]pyrimidine (see Example 1) in 3 ml of abs. THF and the reaction mixture is boiled under reflux for 3 days. The reaction mixture is partitioned between ethyl acetate and saturated Na$_2$CO$_3$ solution and the inorganic phase is separated off and extracted with 2 portions of ethyl acetate. The organic phases are washed 3 times with water and once with brine, dried with MgSO$_4$ and concentrated by evaporation. Digestion with ethyl acetate/diethyl ether yields the title compound; m.p. 247–251° C.; $^1$H-NMR (300 MHz, DMSO-d$_6$): 12.8 and 12.2 (2s, 2H), 8.71 (m, 1H), 8.37 and 8.23 (2s, 2H), 7.93 (m, 1H), 7.80 (d, J=8, 1H), 7.47 (d, J=8, 1H), 7.37 (m, 2H), 7.03 (d, J=8, 1H), 4.18 (s, 2H), 2.40 (s, 6H); MS: (M)$^+$=378.

EXAMPLE 4

4-(3-Chloro-4-fluoro-anilino)-6-(pyrid-2-yl)-7H-pyrrolo[2,3-d]pyrimidine

Under a protective gas, 20 mg (0.09 mmol) of 6-(pyrid-2-yl)-7H-pyrrolo[2,3-d]pyrimidin-4-ol (see Step 1.2) are heated at boiling with 1 ml of phosphorus oxychloride for 30 min. The reaction mixture is concentrated to dryness by evaporation and made into a suspension in 1 ml of n-butanol. 16.4 mg (0.108 mmol) of 3-chloro-4-fluoro-aniline are added and the suspension is boiled under reflux for 2 hours. The dark-brown suspension is then concentrated by evaporation and the residue is dissolved in methanol. Silica gel is added and drying is carried out. The powder is applied to a silica gel column and elution is carried out with ethyl acetate, yielding the title compound; $^1$H-NMR (400 MHz, DMSO-d$_6$): 12.5 (sb, HN), 9.64 (s, HN), 8.64 (d, J=5, 1H), 8.38 (s, 1H), 8.35 (dd, J$_1$=7, J$_2$=3, 1H), 7.92 (m, 2H), 7.83 (m, 1H), 7.53 (s, 1H), 7.41 (t, J=9, 1H), 7.33 (m, 1H); HPLC: t$_{Ret}$(Grad$_{20}$)=10.4 min; MS: (M)$^+$=339.

EXAMPLE 5

4-(3-Chloro-anilino)-5-methyl-6-pyrid-2-yl)-7H-pyrrolo[2,3-d]pyrimidine and 4(3-chloro-anilino)-5-methyl-6-(N-benzyl-pyridinium-2-yl)-7H-pyrrolor[2,3-d]-pyrimidine bromide With the exclusion of air, 529 μl (5.0 mmol) of 3-chloro-aniline are added to approximately 1.2 mmol of 4-chloro-5-methyl-6-(N-benzyl-pyridinium-2-yl)-7H-pyrrolo[2,3-d]-pyrimidine in 10 ml of isopropanol and the reaction mixture is boiled under reflux for 3 hours. The reaction mixture is concentrated by evaporation and the residue is chromatographed over silica gel. Elution with methylene chloride/ethanol (7:3) and methylene chloride/methanol (7:3) yields first 4-(3-chloro-anilino)-5-methyl-6-(pyrid-2-yl)-7H-pyrrolo[2,3-d]pyrimidine (A) and then 4-(3-chloro-anilino)-5-methyl-6-(N-benzyl-pyridinium-2-yl)-7H-pyrrolo[2,3-d] pyrimidine bromide (B). A is also obtained by heating B. A: m.p. 251–252° C.; $^1$H-NMR (200 MHz, DMSO-d$_6$): 12.75 and 9.25 (2sb), 8.75 (d, J=5, 1H), 8.35 (s, 1H), 8.05–7.85 (m, 3H), 7.66 (d, J=8, 1H), 7.45 (m, 2H), 7.29 (d, J=8, 1H), 2.84 (s, 3H); FAB-MS: (M+H)$^+$=336. B: m.p. 171–172° C. (intense foaming); $^1$H-NMR (200 MHz, DMSO-d$_6$): 12.65 (sb), 9.48 (d, J=6, 1H), 8.80 (t, J=8, 1H), 8.59 (sb, 1H), 8.43 (s, 1H), 8.3 (m, 2H), 7.94 (m, 1H), 7.72 (d, J=8, 1H), 7.40 (t, J=8, 1H), 7.28 (m, 3H), 7.17 (d, J=8, 1H), 6.94 (m, 2H), 5.93 (s, 2H), 2.27 (s, 3H); FAB-MS: (M+H)$^+$=426.

The starting material is prepared as follows:

Step 5.1: 2-(5-Amino-4-cyano-3-methyl-1H-pyrrol-2-yl)-N-benzyl-pyridinium bromide Under an argon atmosphere, 1.81 g (5.5 mmol) of N-benzyl-2-bromo-pyridinium bromide [for preparation see J. Heterocyclic Chem. 28,1083 (1991)] are added to 605.5 mg (5.0 mmol) of 2-amino-3-cyano-4-methyl-pyrrole [for preparation see Synthesis (1976), 51] in 40 ml of methylene chloride and 639 μl (5.5 mmol) of lutidine. After 5.5 hours' stirring at RT, the reaction mixture is concentrated by evaporation to approximately half its original volume. Filtering the suspension and washing with methylene chloride/ethyl acetate (1:1) and ethyl acetate/hexane (1:1) yield the title compound; $^1$H-NMR (300 MHz, DMSO-d$_6$): 10.83 (s, 1H), 9.10 (d, J=7, 1H), 8.49 (t, J=7, 1H), 7.96 (m, 2H), 7.30 (m, 3H), 6.95 (m, 2H), 6.57 and 5.80 (2s, each 2H), 1.76 (s, 3H); FAB-MS: (M+H)$^+$=289.

Step 5.2: 5-Methyl-6-(N-benzyl-pyridinium-2-yl)-7H-pyrrolor[2,3-d]pyrimidin-4-ol Under a protective gas, 1.182 g (3.2 mmol) of 2-(5-amino-4-cyano-3-methyl-1H-pyrrol-2-yl)-N-benzyl-pyridinium bromide in 12 ml of formic acid are heated at 110° C. for 90 minutes. The reaction mixture is concentrated by evaporation, the residue is lyophilized from water and, finally, twice from dioxane containing a small amount of water, yielding the title compound; $^1$H-NMR (200 MHz, DMSO-d$_6$): 12.0 (sb), 9.40 (d, J=8, 1H), 8.73 (t, J=8, 1H), 8.25 (m, 2H), 7.98 (s, 1H), 7.27 (m, 3H), 6.90 (m, 2H), 5.92 (s, 2H), 2.04 (s, 3H); HPLC t$_{Ret}$(20)=5.8 min; FAB-MS: (M+H)$^+$=317.

Step 5.3: 4-Chloro-5-methyl-6-(N-benzyl-pyridinium-2-yl)-7H-pyrrolo[2,3-dipyrimidine With the exclusion of moisture, 500 mg (1.2 mmol) of 5-methyl-6-(N-benzyl-pyridinium-2-yl)-7H-pyrrolo[2,3-d] pyrimidin-4-ol and 15 ml of phosphorus oxychloride are heated at boiling for 2 hours. Concentration of the reaction mixture by evaporation yields the title compound; HPLC: t$_{Ret}$(Grad$_{20}$)=8.8 min; FAB-MS: (M+H)$^+$=335.

EXAMPLE 6
4-(3-Chloro-4-fluoro-anilino)-5-methyl-6-(pyrid-2-yl)-7H-pyrrolor[2,3-d]-pyrimidine The title compound is obtained analogously to Example 5 with 3-chloro-4-fluoro-aniline; m.p. 277–278° C.; $^1$H-NMR (300 MHz, DMSO-$d_6$): 9.3 (sb), 8.73 (d, J=5, 1H), 8.33 (s, 1H), 7.96 (m, 2H), 7.88 (d, J=8, 1H), 7.67 (m, 1H), 7.52 (t, J=9, 1H), 7.40 (m, 1H), 2.83 (s, 3H); MS: (M)$^+$=353.

EXAMPLE 7
4-(3-Chloro-anilino)-7H-pyrrolo[2,3-d]pyrimidine 133 mg (0.866 mmol) of 4-chloro-7H-pyrrolo[2,3-d]pyrimidine [for preparation see: Chem. Ber. 112, 3526 (1979)] and 136 μl (1.3 mmol) of 3-chloro-aniline are heated at boiling in 4 ml of n-butanol for 90 min. The dark-green reaction solution is diluted with ethanol and filtered while hot through activated carbon. Concentration by evaporation, stirring in isopropanol, filtering and recrystallization from hot isopropanol containing a small amount of ethanol yield the title compound; m.p. 230–233° C.; 12.5 and 10.7 (2sb, 2H), 8.42 and 7.97 (2s, 2H), 7.67 (d, J=8, 1H), 7.48 (t, J=8, 1H), 7.43 (m, 1H), 7.29 (d, J=8, 1H), 6.93 (sb, 1H); FAB-MS: (M+H)$^+$=245.

EXAMPLE 8
4-(3-Chloro-anilino)-6-(biphen-4-yl)-7H-pyrrolo[2,3-d]pyrimidine

A suspension of 220 mg (0.72 mmol) of 4-chloro-6-(biphen-4-yl)-7H-pyrrolo[2,3-d]-pyrimidine and 151 μl (1.44 mmol) of 3-chloro-aniline in 5 ml of butanol is heated at boiling overnight. Cooling, filtering and washing with a large amount of ethanol and, finally, hexane yield the title compound; $^1$H-NMR (200 MHz, DMSO-$d_6$): 12.46 (sb, 1H), 9.6 (s, 1H), 8.40 (s, 1H), 8.28 (m, 1H), 7.98 (d, J=8, 2H), 7.8 (m, 5H), 7.52 and 7.38 (2t, J=8, each 2H), 7.30 (s, 1H), 7.08 (db, J=8, 1H); MS: (M)$^+$=397.

The starting material is prepared as follows:
Step 8.1: 2-Amino-3-ethoxycarbonyl-5-(biphen-4-yl)-1H-pyrrole Under an argon atmosphere, 1.65 g (1 0 mmol) of 2-amidino-acetic acid ethyl ester hydrochloride (for preparation see: *Liebigs Ann. Chem.*, 1895 (1977)) are introduced into 10 ml of ethanol and, at 0–5° C., 0.73 g (10 mmol) of sodium ethanolate is added thereto. The bright yellow suspension is stirred for 20 min and then 1.4 g (5 mmol) of 2-bromo-1-(biphen-4-yl)-ethan-1-one (2-bromo-4'-phenyl-acetophenone; Aldrich; Milwaukee/USA) are added thereto. After 48 hours' stirring at RT, the reaction mixture is concentrated by evaporation and the residue is taken up in ethyl acetate and washed with 3 portions of water and brine. The aqueous phases are extracted twice with ethyl acetate and the organic phases are dried over $MgSO_4$ and concentrated by evaporation. Column chromatography ($SiO_2$; ethyl acetate/hexane [1:1]) and stirring in diisopropyl ether/hexane yield the title compound; m.p. 186–188° C.; TLC-$R_f$=0.17 (ethyl acetate/hexane [1:1]); FAB-MS: (M+H)$^+$=306.

Step 8.2: 6-(Biphen-4-yl)-7H-pyrrolo[2,3-d]pyrimidin-4-ol
766 mg (2.5 mmol) of 2-amino-3-ethoxycarbonyl-5-(biphen-4-yl)-1H-pyrrole are stirred in 5 ml of formamide, 2.5 ml of DMF and 1.25 ml of formic acid for 20 h at 150° C. The reaction mixture is diluted with isopropanol and filtered. Washing with isopropanol and hexane yields the title compound; m.p.>300° C.; FAB-MS: (M+H)$^+$=288.

Step 8.3: 4-Chloro-6-(biphen-4-yl)-7H-pyrrolo[2,3-d]pyrimidine

Under a protective gas, 430.5 mg (1.5 mmol) of 6-(biphen-4-yl)-7H-pyrrolo[2,3-d]-pyrimidin-4-ol in 6 ml of phosphorus oxychloride are heated at boiling for 4 hours. The reaction mixture is poured into ice-water and ethyl acetate. The aqueous phase is separated off and extracted with ethyl acetate. Concentrating the organic phases by evaporation and stirring the residue in hot THF/isopropanol yield the title compound; m.p. 295–300° C. (decomposition); FAB-MS: (M+H)$^+$=306.

EXAMPLE 9
4-(3-Chloro-anilino)-6-(naphth-2-yl)-7H-pyrrolor[2,3-d]pyrimidine 98 mg (0.35 mmol) of 4-chloro-6-(naphth-2-yl)-7H-pyrrolo[2,3-d]pyrimidine and 73 μl (0.7 mmol) of 3-chloro-aniline in 8 ml of butanol are heated at boiling for 5 hours. Cooling, filtering and washing with isopropanol and hexane yield the title compound; m.p. 278–284° C.; TLC-$R_f$=0.5 (ethyl acetate/hexane [1:1]); FAB-MS: (M+H)$^+$=371.

The starting material is prepared as follows:
Step 9.1: 2-Amino-3-ethoxycarbonyl-5-(naphth-2-yl)-1H-pyrrole Under an argon atmosphere, 834 mg (5 mmol) of 2-amidino-acetic acid ethyl ester hydrochloride [for preparation see: Liebigs Ann. Chem., 1895 (1977)] are introduced into 10 ml of ethanol and, at 0–5° C., 358 mg (5 mmol) of sodium ethanolate are added thereto. The bright yellow suspension is stirred for 15 min and then 623 mg (2.5 mmol) of 2-bromo-1-(naphth-2-yl)-ethan-1-one (2-bromo-2'-acetonaphthone; Aldrich; Milwaukee/USA) are added thereto. After 3 days' stirring at RT, the reaction mixture is concentrated by evaporation. The residue is taken up in ethyl acetate/water and filtered and the organic phase is separated off and washed with 3 portions of water and brine. The aqueous phases are extracted with ethyl acetate and the organic phases are dried over $MgSO_4$ and concentrated by evaporation. Column chromatography ($SiO_2$; ethyl acetate/hexane [1:1]) and stirring in diethyl ether/hexane yield the title compound; m.p. 149–151° C.; TLC-$R_f$=0.5 (ethyl acetate/hexane [1:1]); FAB-MS: (M+H)$^+$=281.

Step 9.2: 6-(Naphth-2-yl)-7H-pyrrolo[2,3-d]pyrimidin-4-ol 420 mg (1.5 mmol) of 2-amino-3-ethoxycarbonyl-5-(naphth-2-yl)-1H-pyrrole are stirred in 3 ml of formamide, 1.5 ml of DMF and 0.75 ml of formic acid at 150° C. for 22 hours. The reaction mixture is diluted with approximately 1 ml of isopropanol and filtered. Washing with ethanol, isopropanol and hexane yields the title compound; m.p.>300° C.; $^1$H-NMR (200 MHz, DMSO-$d_6$): 12.2 (sb), 8.39 (s, 1H), 8.0 (m, 2H), 7.9 (m, 3H), 7.53 (m, 2H), 7.11 (s, 1H).

Step 9.3: 4-Chloro-6-(naphth-2-yl)-7H-pyrrolo[2,3-d]pyrimidine

Under a protective gas, 198.5 mg (0.76 mmol) of 6-(naphth-2-yl)-7H-pyrrolo[2,3-d]-pyrimidin-4-ol in 3 ml of phosphorus oxychloride are heated at boiling for 5 hours. The reaction mixture is poured into ice-water and stirred for 1 hour to complete the reaction. The crystals are filtered off and washed with water. Dissolving the crude product in THF/methanol, filtering through active carbon, concentrating the filtrate by evaporation, stirring the residue in isopropanol and washing with hexane yield the title compound; m.p. 268–269° C. (decomposition); FAB-MS: (M+H)$^+$=280.

EXAMPLE 10
4-(3-Chloro-anilino)-6-(2-hydroxy-phenyl)-7H-pyrrolor[2,3-d]pyrimidine hydrobromide In a dry apparatus, under an argon atmosphere, 6.72 g (19.16 mmol) of 4-(3-chloro-anilino)-6-(2-methoxy-phenyl)-7H-pyrrolo[2,3-d]pyrimidine are introduced into 150 ml of methylene chloride. There is added dropwise thereto in the course of 1 hour, with ice-cooling, a solution of 18.4 ml (191.6 mmol) of boron tribromide in 100 ml of methylene chloride. After 3 hours' stirring in an ice-bath, the suspension is poured into 0.5 liter of ice-water and filtered. The residue is taken up in ethyl acetate and washed with saturated $NaHCO_3$ solution, water and brine. The aqueous phases are extracted twice with ethyl acetate and the organic phases are dried over $MgSO_4$, concentrated by evaporation and crystallized from ethanol/hexane, yielding the title compound; $^1$H-NMR (300 MHz, DMSO-$d_6$): 8.41 (s, 1H), 7.92 (s, 1H), 7.78 (d, J=8, 1H), 7.64 (d, J=8, 1 H), 7.50 (m, 2H), 7.35 (d, J=8, 1H), 7.23 (m, 1H), 7.04 (d, J=8, 1H), 6.95 (dd, J=8, 1 H); FAB-MS: $(M+H)^+$=337.

The starting material is prepared as follows:

Step 10.1: 2-Amino-3-ethoxycarbonyl-5-(2-methoxy-phenyl)-1H-pyrrole

Analogously to Step 8.1, 14.5 g (87 mmol) of 2-amidino-acetic acid ethyl ester hydrochloride in 150 ml of abs. ethanol are reacted with 5.9 g (87 mmol) of sodium ethanolate and 10.3 g (44 mmol) of 2-bromo-1-(2-methoxy-phenyl)-ethan-1-one (2-bromo-2'-methoxy-acetophenone; Aldrich; Milwaukee/USA) to form the title compound; m.p.: 128° C.; TLC-$R_f$=0.25 (hexane/ethyl acetate [2:1]).

Step 10.2: 6-(2-Methoxy-phenyl)-7H-pyrrolor[2,3-d]pyrimidin-4-ol

Under a protective gas, 7.66 g (31 mmol) of 2-amino-3-ethoxycarbonyl-5-(2-methoxy-phenyl)-1H-pyrrole in 63 ml of formamide, 31.5 ml of DMF and 17.7 ml of formic acid are heated at 150° C. overnight. Working-up analogously to Step 8.2 yields the title compound; TLC-$R_f$=0.33 (hexane/ethyl acetate [1:1]).

Step 10.3: 4-Chloro-6-(2-methoxy-phenyl)-7H-pyrrolo[2,3-d]pyrimidine

Under argon, 6.2 g (25.7 mmol) of 6-(2-methoxy-phenyl)-7H-pyrrolo[2,3-d]pyrimidin-4-ol and 62 ml of phosphorus oxychloride are heated at 125° C. for 1.5 hours. The reaction mixture is poured into ice-water and extracted three times with ethyl acetate. The organic phases are washed with water, $NaHCO_3$ solution and brine, dried with $MgSO_4$ and concentrated by evaporation. Filtering through a silica gel column with ethyl acetate yields the title compound; TLC-$R_f$=0.8 (hexane/ethyl acetate [1:1]).

Step 10.4: 4-(3-Chloro-anilino)-6-(2-methoxy-phenyl)-7H-pyrrolo[2,3-d]pyrimidine 6.6 g (25.4 mmol) of 4-chloro-6-(2-methoxy-phenyl)-7H-pyrrolo[2,3-d]pyrimidine and 5.34 ml (50.8 mmol) of 3-chloro-aniline in 100 ml of n-butanol are heated at boiling for 1.5 hours. The reaction mixture is cooled, then filtered and washed with diethyl ether and hexane. Flash chromatography ($SiO_2$; applied dry; hexane/ethyl acetate [2:1] ethanol/acetone [1:1]) yields the title compound; m.p. 221–222° C.; TLC-$R_f$=0.3 (hexane/ethyl acetate [1:1]); FAB-MS: $(M+H)^+$=351.

EXAMPLE 11

4-(3-Chloro-anilino)-6-(3-hydroxy-phenyl)-7H-pyrrolor[2,3-d]-pyrimidine hydrobromide Analogously to Example 10, 4.53 g (12.91 mmol) of 4-(3-chloro-anilino)-6-(3-methoxy-phenyl)-7H-pyrrolo[2,3-d]pyrimidine in 150 ml of methylene chloride are reacted with 12.4 ml (129 mmol) of boron tribromide in 150 ml of methylene chloride to form the title compound; HPLC: $t_{Ret}$(Grad$_2$O)=10.5 min; $^1$H-NMR (500 MHz, DMSO-$d_6$): 12.61, 10.07 and 9.68 (3sb, 3H), 8.35 (s, 1H), 8.09 (s, 1H), 7.76 (d, J=8, 1H), 7.39 (dd, J=8, 1H), 7.27 (m, 2H), 7.23 (s, 1H), 7.12 (1H), 7.11 (s, 1H), 6.77 (m, 1H).

The starting material is prepared as follows:

Step 11.1: 2-Amino-3-ethoxycarbonyl-5-(3-methoxy-phenyl)-1H-pyrrole

Analogously to Step 8.1, 14.5 g (87 mmol) of 2-amidino-acetic acid ethyl ester hydro-chloride in 150 ml of abs. ethanol are reacted with 5.9 g (87 mmol) of sodium ethanolate and 10.3 g (44 mmol) of 2-bromo-1-(3-methoxy-phenyl)-ethan-1-one (2-bromo-3'-methoxy-acetophenone; Janssen) to form the title compound; m.p. 96–97oC; TLC-$R_f$=0.2 (hexane/ethyl acetate [2:1]).

Step 11.2: 6-(3-Methoxy-phenyl)-7H-pyrrolo[2,3-d]pyrimidin-4-ol

Under a protective gas, 7.19 g (29 mmol) of 2-amino-3-ethoxycarbonyl-5-(3-methoxy-phenyl)-1H-pyrrole in 59 ml of formamide, 29.5 ml of DMF and 14.7 ml of formic acid are heated at 150° C. overnight. Working-up analogously to Step 8.2 yields the title compound; TLC-$R_f$=0.3 (hexane/ethyl acetate [1:1]).

Step 11.3: 4-Chloro-6-(3-methoxy-phenyl)-7H-pyrrolo[2,3-d]pyrimidine With the exclusion of moisture, 5.28 g (21.9 mmol) of 6-(3-methoxy-phenyl)-7H-pyrrolo[2,3-d]pyrimidin-4-ol and 53 ml of phosphorus oxychloride are heated at boiling for 1.5 hours. The reaction mixture is cooled and filtered. The residue is dissolved in ethyl acetate and washed with $NaHCO_3$ solution, water and brine. The aqueous phases are extracted once with ethyl acetate, dried with $MgSO_4$ and concentrated by evaporation to form the title compound; TLC-$R_f$=0.73 (hexane/ethyl acetate [1:1]).

Step 11.4: 4-(3-Chloro-anilino)-6-(3-methoxy-phenyl)-7H-pyrrolor[2,3-d]pyrimidine 5.68 g (21.9 mmol) of 4-chloro-6-(3-methoxy-phenyl)-7H-pyrrolo[2,3-d]pyrimidine and 4.59 ml (43.7 mmol) of 3-chloro-aniline in 75 ml of n-butanol are heated at boiling for 1.5 hours. Working-up analogously to Step 10.4 yields the title compound; m.p. 262–263° C.; FAB-MS: $(M+H)^+$=351.

EXAMPLE 12

4-(3-Chloro-anilino)-6-(4-hydroxy-phenyl)-7H-pyrrolo[2,3-d]pyrimidine hydrobromide With the exclusion of moisture, at approximately 0° C., 6 ml of boron tribromide in 100 ml of methylene chloride are added within the course of 40 min to 2.0 g (5.7 mmol) of 4-(3-chloro-anilino)-6-(4-methoxy-phenyl)-7H-pyrrolo[2,3-d]pyrimidine in 60 ml of methylene chloride. After 21 hours' stirring at RT the reaction mixture is filtered. The crude product is precipitated from the filtrate with approximately 1 liter of hexane, filtered off and washed with hexane. The residue is taken up in 0.2 liter of water and 0.6 liter of ethyl acetate and rendered neutral with 5% $NaHCO_3$ solution. The organic phase is separated off, washed with water and brine, dried over $MgSO_4$ and concentrated by evaporation. Crystallization from hot methanol with hexane yields the title compound; analysis calculated for $C_{18}H_{14}N_4OBrCl$ (+0.13 $H_2O$): C 51.47%, H 3.36%, N 13.34%, Br 19.02%, Cl 8.44%; found: C 51.58%, H 3.32%, N 13.37%, Br 19.29%, Cl 8.46%; $^1$H-NMR (360 MHz, DMSO-$d_6$): 12.85 and 10.60 (2sb, 2H), 10.5–9.5 (sb), 8.37 (s, 1H), 7.92 (s, 1H), 7.67 (d, J=8, 2H), 7.63 (d, J=8, 1H), 7.51 (dd, J=8, 1 H), 7.33 (d, J=8, 1H), 7.06 (s, 1H), 6.90 (d, J=8, 2H).

The starting material is prepared as follows:

Step 12.1: 2-Amino-3-ethoxycarbonyl-5-(4-methoxy-phenyl)-1H-pyrrole

Analogously to Step 8.1, 1.67 g (10 mmol) of 2-amidino-acetic acid ethyl ester hydro-chloride in 20 ml of abs. ethanol are reacted with 716 mg (10 mmol) of sodium ethanolate and 1.145 g (5.0 mmol) of 4-methoxy-phenacyl bromide (Fluka; Buchs/Switzerland) to form the title compound; m.p. 141–142° C.; TLC-$R_f$=0.4 (hexane/ethyl acetate [1:1]); FAB-MS: $(M+H)^+$=261.

Step 12.2: 6-(4-Methoxy-phenyl)-7H-pyrrolo[2,3-d]pyrimidin-4-ol

Under a protective gas, 611 mg (2.3 mmol) of 2-amino-3-ethoxycarbonyl-5-(4-methoxy-phenyl)-1H-pyrrole in 5 ml of formamide, 2.5 ml of DMF and 1.25 ml of formic acid are heated at 150° C. overnight. Working-up analogously to Step 8.2 yields the title compound; m.p.>300° C.; FAB-MS: (M+H)$^+$=242.

Step 12.3: 4-Chloro-6-(4-methoxy-phenyl)-7H-pyrrolo[2,3-d]pyrimidine

With the exclusion of moisture, 121 mg (0.50 mmol) of 6-(4-methoxy-phenyl)-7H-pyrrolo[2,3-d]pyrimidin-4-ol and 1 ml of phosphorus oxychloride are heated at boiling for 1.5 hours. The reaction mixture is poured into ice-water and extracted twice with ethyl acetate. The organic phases are washed three times with water and brine, dried with MgSO$_4$ and concentrated by evaporation. Stirring of the residue in diethyl ether yields the title compound; m.p. 248-249OC; FAB-MS: (M+H)$^+$=260.

Step 12.4: 4-(3-Chloro-anilino)-6-(4-methoxy-phenyl)-7H-pyrrolor[2,3-d]pyrimidine A solution of 95 mg (0.365 mmol) of 4-chloro-6-(4-methoxy-phenyl)-7H-pyrrolo[2,3-d]-pyrimidine and 77 μl (0.732 mmol) of 3-chloro-aniline in 3 ml of n-butanol and a few drops of DMPU is heated at boiling for 2 hours. The reaction mixture is cooled, diluted with diethyl ether and isopropanol and filtered; m.p. 294–295° C.; FAB-MS: (M+H)$^+$=351.

EXAMPLE 13

4-(3-Chloro-anilino)-5-dimethylaminomethyl-6-(4-hydroxy-phenyl)-7H-pyrrolo[2,3-d]pyrimidine Under an argon atmosphere, 96.2 mg (0.52 mmol) of N,N-dimethyl-methyleneimmonium iodide (Fluka; Buchs/Switzerland) are added to 134.7 mg (0.40 mmol) of 4-(3-chloro-anilino)-6-(4-hydroxy-phenyl)-7H-pyrrolo[2,3-d]pyrimidine in 4.8 ml of abs. THF and the reaction mixture is boiled under reflux for 1.5 hours. Working-up as described in Example 3 and recrystallization from hot ethanol yield the title compound; m.p. 269–271° C.; TLC-R$_f$=0.31 (CH$_2$Cl$_2$/methanol [10:1]); MS: (M)$^+$=393; $^1$H-NMR (500 MHz, DMSO-d$_6$): 12.48,11.91 and 9.75 (3s, 3H), 8.32 and 8.25 (2s, 2H), 7.40 (d, J=8, 1H), 7.34 (1H), 7.32 (d, J=8, 2H), 7.00 (d, J=8, 1H), 6.89 (d, J=8, 2H), 3.72 (s, 2H), 2.36 (s, 6H).

EXAMPLE 14

4-(3-Chloro-anilino)-5-dimethylaminomethyl-6-phenyl-7H-pyrrolor[2,3-d]pyrimidine Under an argon atmosphere, 898.2 mg (2.80 mmol) of 4-(3-chloro-anilino)-6-phenyl-7H-pyrrolo[2,3-d]pyrimidine in 33.6 ml of abs. THF are boiled under reflux overnight with 673.4 mg (3.64 mmol) of N,N-dimethyl-methyleneimmonium iodide (Fluka; Buchs/Switzerland). The reaction mixture is partitioned between ethyl acetate and 1N (=one normal) hydrochloric acid. The organic phase is separated off and washed three times with water. The aqueous phases are back-extracted once with ethyl acetate and rendered basic with solid sodium carbonate, resulting in a suspension to which ethyl acetate is added, whereupon the solid becomes concentrated in the organic phase. The organic phase is washed neutral with water three times and the aqueous phases are back-extracted with ethyl acetate. The combined organic phases (suspensions) are concentrated by evaporation. Stirring the residue in diethyl ether yields the title compound; MS: (M)$^+$=377; $^1$H-NMR (200 MHz, DMSO-d$_6$): 12.57 and 12.12 (2s, 2H), 8.38 (s, 1H), 8.29 (m, 1H), 7.55 (m, 4H), 7.5–7.3 (m, 3H), 7.04 (dm, J=8, 1H), 3.79 (s, 2H), 2.38 (s, 6H).

The starting material is prepared as follows:

Step 14.1: 6-Phenyl-7H-pyrrolo[2,3-d]pyrimidin-4-ol

Under a protective gas, 2.30 g (10 mmol) of 2-amino-3-ethoxycarbonyl-5-phenyl-1H-pyrrole [for preparation see: Synthesis, 272 (1987)] in 20 ml of formamide, 10 ml of DMF and 5 ml of formic acid are heated at 150° C. for 24 hours. The reaction mixture is cooled and filtered and the residue is washed with isopropanol/hexane. Stirring in hot isopropanol yields the title compound; m.p.>300° C.; FAB-MS: (M+H)$^+$=212.

Step 14.2: 4-Chloro-6-phenyl-7H-pyrrolo[2,3-d]pyrimidine

With the exclusion of moisture, 1.795 g (8.5 mmol) of 6-phenyl-7H-pyrrolo[2,3-d]-pyrimidin-4-ol and 27 ml of phosphorus oxychloride are heated at boiling for 3 hours. Pouring the reaction mixture into ice-water, filtering and washing with hot isopropanol and hexane yield the title compound; FAB-MS: (M+H)$^+$=230.

Step 14.3: 4-(3-Chloro-anilino)-6-phenyl-7H-pyrrolo[2,3-d]pyrimidine

A suspension of 1.251 g (5.45 mmol) of 4-chloro-6-phenyl-7H-pyrrolo[2,3-d]pyrimidine and 1.15 ml (10.9 mmol) of 3-chloro-aniline in 20 ml of n-butanol and 0.5 ml of DMPU is heated at boiling for 2 hours. The reaction mixture is cooled and filtered. Stirring of the residue in hot THF/methanol yields the title compound; m.p. 285–286° C.; FAB-MS: (M+H)$^+$=321.

EXAMPLE 15 (Reference Example)

4-(3-Chloro-anilino)-pyrimido[4,5-b]indole

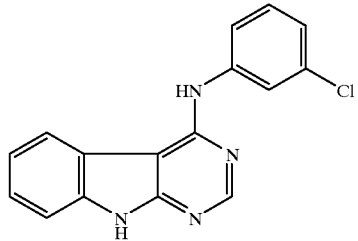

5.7 g (15 mmol) of N-benzyl-4-(3-chloro-anilino)-pyrimido[4,5-b]indole are added to a suspension of 7.6 g of anhydrous AlCl$_3$ in 50 ml of toluene and the reaction mixture is heated at 100° C. for 45 min. The reaction mixture is cooled to RT, poured into ice-water and stirred for approximately 30 min, the crude product precipitating. The crude product is filtered off with suction and washed with water. The filtrate is discarded. The crude product is dissolved in THF/ethyl acetate, washed with 5% sodium hydrogen carbonate solution and then with saturated NaCl solution, dried and concentrated. Crystals of 4-(3-chloro-anilino)-pyrimido[4,5-b]indole precipitate when left to stand in a refrigerator. The product is precipitated out completely with cyclohexane. Further purification is effected by digestion in ethyl acetate. The title compound is obtained in the form of slightly pink-colored crystals; m.p.>260° C.; $^1$H-NMR (360 MHz, DMSQ-d$_6$): 12.20 (s, pyrrole NH), 8.97 (s, aniline NH), 7.1-8.5 (m, 8 aromatic H +pyrimidine H); FAB-MS: (M+H)$^+$=295.

HCl salt 2.8 g of 4-(3-chloro-anilino)-pyrimido[4,5-b]indole are dissolved while hot in 400 ml of THF and cooled to RT and, with stirring, 2.8 ml of a 5-molar solution of HCl in diethyl ether are added thereto. After the addition of approximately 250 ml of diethyl ether and cooling in an ice-bath, 4-(3-chloro-anilino)-pyrimido[4,5-b]indole hydrochloride precipitates in the form of colorless crystals having a m.p. of 280–286° C.

The starting material is prepared as follows:

Step 15.1: 4-Hydroxy-5,6-tetramethylene-7-benzyl-pyrrolor[2,3-d]pyrimidine 15 g of 2-amino-1-benzyl-3-cyano-4,5,6,7-tetrahydroindole (prepared from 2-hydroxy-cyclohexanone, benzylamine and malonodinitrile using a known method (see H. J. Roth and K. Eger, Arch. Pharmaz. 308, 179 [1975])) are boiled with 100 ml of 85% formic acid at 110° C. for 5 hours. The reaction solution is cooled in an ice-bath, light-brown crystals precipitating. The suspension is poured into approximately 200 ml of ice-water and stirred for approximately 10 min. The precipitate is then filtered off with suction. The crystals are washed with water and then with hexane and dried, yielding the title compound having a m.p. of 104–105° C; FAB-MS: $(M+H)^+=280$.

Step 15.2: 4-(3-Chloro-anilino)-5,6-tetramethylene-7-benzyi-pyrrolor[2,3-d]pyrimidine 0.65 g of 4-chloro-5,6-tetramethylene-7-benzyl-pyrrolo[2,3-d]pyrimidine and 0.27 ml of 3-chloro-aniline in 10 ml of ethanol are heated under reflux for 17 hours. The brown solution is concentrated to dryness by evaporation, the residue is taken up in ethyl acetate, the ethyl acetate solution is washed neutral with sodium hydrogen carbonate solution and water, dried and concentrated by evaporation. The residue is crystallised from ethyl acetate/hexane. The title compound is obtained in the form of white crystals having a m.p. of 145–147° C.; FAB-MS: $(M+H)^+=389$.

Step 15.3: N-Benzyl-4-(3-chloro-anilino)-pvrimido[4,5-b]indole 14.1 g (62 mmol) of 2,3-dichloro-5,6-dicyano-1,4-benzoquinone (DDQ) are added to a solution of 12.1 g (31 mmol) of 4-(3-chloro-anilino)-5,6-tetramethylene-7-benzyl-pyrrolo[2,3-d]pyrimidine in 260 ml of toluene. The deep-red solution is heated under reflux for 30 min and then cooled to RT. Insoluble material is filtered off and the filtrate is concentrated by evaporation using a rotary evaporator. The crude product is chromatographed on silica gel (elution with hexane/ethyl acetate), yielding colourless crystals of the title compound having a m.p. of 174–176° C.; $^1$H-NMR (360 MHz, CDCl$_3$): 12.20 (s, pyrrole NH), 9.0 (s, aniline H), 7.0–8.6 (m, 13 aromatic H and 1 pyrimidine H), 5.66 (s, 2H, benzyl group); FAB-MS: $(M+H)^+=385$.

EXAMPLE 16

4-(3-Chloro-anilino)-5-methyl-6-(4-hydroxy-phenyl)-7H-pyrrolo-[2,3-d]pyrimidine hydrobromide The title compound, in the form of a colourless powder, is obtained analogously to Example 10 by removing the methyl group from 5 g (6.85 mmol) of 4-(3-chloro-anilino)-5-methyl-6-(4-methoxy-phenyl)-7H-pyrrolo[2,3-d]pyrimidine with 4.4 g of boron tribromide in 30 ml of methylene chloride; m.p.: 295–296° C.; $^1$H-NMR (360 MHz, DMSO-d$_6$): 11.85 (s, pyrrole NH), 9.68 (s, phenolic H), 8.29 (s, aniline NH), 8.27 (s, pyrimidine H), 7.94 (m, aromat. H), 7.70 (m, aromat. H), 7.42 (d, 2 aromat. H), 7.35 (t, aromat. H), 7.06 (m, aromat. H), 6.90 (d, 2 aromat. H), 2.58 (s, 3H); FAB-MS: $(M+H)^+=351$.

HCl salt

For the preparation of the HCl salt, 600 mg of 4-(3-chloro-anilino)-5-methyl-6-(4-hydroxy-phenyl)-7H-pyrrolo[2,3-d]pyrimidine hydrobromide are dissolved while hot in 50 ml of ethyl acetate and at RT adjusted to pH 9.5 with 1 N NaOH and the organic phase is washed twice with water. The organic phase is dried and concentrated by evaporation, and the residue is dissolved in 30 ml of ethanol, and a 5N (=5 normal) ethanolic HCl solution is added thereto. At 0° C., with stirring and the addition of diethyl ether, 4-(3-chloro-anilino)-5-methyl-6-(4-hydroxyphenyl)-7H-pyrrolo[2,3-d]pyrimidine hydrochloride is obtained in the form of a colourless powder having a m.p. of 280–282° C.

The starting material is prepared as follows:

Step 16.1: 4-Chloro-5-methyl-6-(4-methoxy-phenyl)-7H-pyrrolo[2,3-d]pyrimidine

Analogously to Step 1.3, the title compound is obtained from 4-hydroxy-5-methyl-6-(4-methoxy-phenyl)-7H-pyrrolo[2,3-d]pyrimidine by boiling in phosphorus oxychloride; FAB-MS: $(M+H)^+=274$.

Step 16.2: 4-(3-Chloro-anilino)-5-methyl-6-(4-methoxy-phenyl)-7H-pyrrolo[2,3-d]-pyrimidine 4 g of 4-chloro-5-methyl-6-(4-methoxy-phenyl)-7H-pyrrolo[2,3-d]pyrimidine and 8.45 ml of 3-chloro-aniline are heated under reflux in 400 ml of n-butanol for 20 hours. The brown solution is concentrated, the desired product already precipitating. The solution is stored overnight in a refrigerator and the product is filtered off with suction and washed with hexane/ethyl acetate, yielding the title compound in the form of colourless crystals; m.p. 265–268° C.; FAB-MS: $(M+H)^+=365$.

EXAMPLE 17

4-(3-Chloro-anilino)-6-(4-nitro-phenyl)-7H-pyrrolo[2,3-d]pyrimidine

The title compound, in the form of rust-brown crystals, is obtained analogously to Example 5 by boiling 0.25 g (0.91 mmol) of 4-chloro-6-(4-nitro-phenyl)-7H-pyrrolo-[2,3-d]pyrimidine with 0.19 ml of 3-chloro-aniline in 5 ml of n-butanol; m.p.:>250° C.; $^1$H-NMR (360 MHz, DMSO-d$_6$): 12.95 (s, pyrrole NH), 10.3 (s, aniline NH), 8.45 (s, pyrimidine H), 8.24 (s, aromat. H), 7.18–8.4 (7 aromat. H +pyrrole 5H); MS: $(M)^+=365$.

The starting material is prepared as follows:

Step 17.1: 2-Amino-3-ethoxycarbonyl-5-(4-nitro-phenyl)-pyrrole

In a dry three-necked flask, under argon, 75 ml of abs. ethanol and 6.5 g (390 mmol) of 2-amidino-acetic acid ethyl ester hydrochloride [for preparation see: Liebigs Ann. Chem., 1895 (1977)] are cooled to 0–5° C. and 2.65 g (390 mmol) of sodium ethanolate are added thereto. Then 5 g (195 mmol) of 2-bromo-1-(4-nitro-phenyl)-ethan-1-one are added and the reaction mixture is allowed to come to RT and then stirred for 48 hours. The reaction mixture is then partitioned between water and ethyl acetate. The ethyl acetate phase is washed three times with water and once with saturated NaCl solution, dried and filtered and the filtrate is concentrated by evaporation. The red-brown residue is suspended in hexane and the title compound precipitates in the form of the crude product (purity 93%), which is used for the next step without further purification; MS: $(M)^+=275$.

Step 17.2: 4-Hydroxy-6-(4-nitro-phenyl)-7H-pyrrolo[2,3-d]pyrimidine 2.5 g (97 mmol) of 2-amino-3-ethoxycarbonyl-5-(4-nitro-phenyl)-pyrrole, 19.4 ml of formamide, 9.7 ml of DMF and 3.1 ml of formic acid are stirred together at 150° C. for 22 hours. 1 ml of isopropanol is added to the hot reaction mixture. The reaction mixture is cooled and the product that has precipitated is filtered off. The product is washed in succession three times with 10 ml of ethanol each time, twice with 10 ml of isopropanol each time and twice with 10 ml of hexane each time, yielding the title compound in the form of rust-brown crystals which are used for the next step; MS: $(M)^+=256$.

Step 17.3: 4-Chloro-6-(4-nitro-phenyl)-7H-pyrrolo[2,3-d]pyrimidine

Analogously to Step 1.3, 4-chloro-6-(4-nitro-phenyl)-7H-pyrrolo[2,3-d]pyrimidine is prepared by heating 4-hydroxy-6-(4-nitro-phenyl)-7H-pyrrolo[2,3-d]pyrimidine with POCl$_3$ (purity 93%); m.p.>280° C.; FAB-MS: (M+H)$^+$=275.

EXAMPLE 18
4-(3-Chloro-anilino)-6-(4-amino-phenyl)-7H-pyrrolor[2,3-d]pyrimidine 150 mg (0.41 mmol) of 4-(3-chloro-anilino)-6-(4-nitro-phenyl)-7H-pyrrolo[2,3-d]pyrimidine are hydrogenated for 5 hours with 50 mg of Raney nickel in 20 ml of THF/methanol at RT and under normal pressure, the desired product already precipitating. The catalyst is filtered off and the filter residue is washed with hot THF. The filtrate is concentrated to dryness by evaporation. The crude product is purified by being digested several times in methanol and being precipitated from THF/hexane, yielding the title product in the form of light-beige crystals; m.p.>290° C., $^1$H-NMR (360 MHz, DMSO-d$_6$): 12.05 (s, pyrrole NH), 9.38 (s, aniline NH), 8.31 (s, pyrimidine H), 8.24 (s, aromat. H), 7.80 (d, aromat. H), 7.53 (d, 2 aromat. H), 7.35 (t, aromat. H), 7.05 (d, aromat. H), 6.90 (s, pyrrole 5H), 6.64 (d, 2 aromat. H), 5.35 (s, NH$_2$); MS: (M)$^+$=335.

EXAMPLE 19
4-(3-Chloro-phenylamino)-9H-pyrido[3',2':4,5]pyrrolo[2,3-d]pyrimidine

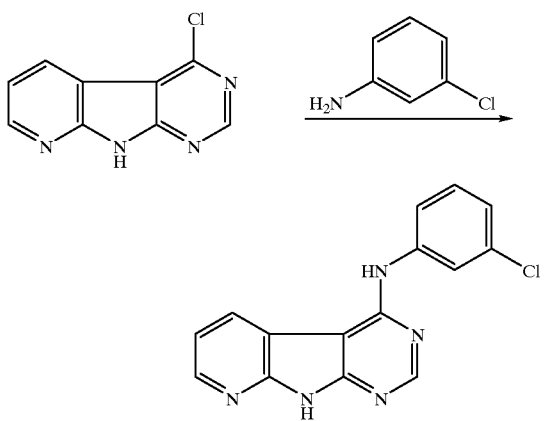

With stirring under a nitrogen atmosphere, a mixture of 0.034 g (0.166 mmol) of 4-chloro-9H-pyrido[3',2':4,5]pyrrolo[2,3-d]pyrimidine (German Offenlegungsschrift No. 1916050) and 0.524 ml (4.99 mmol) of 3-chloro-aniline is heated at 120° C. for 1 hour. The reaction mixture is cooled to room temperature and then 5 ml of ethanol are added thereto. After further cooling to 0° C., the reaction mixture is filtered and the crystals are washed with ethanol and dried under a high vacuum. The resulting title compound melts at >260° C., El-MS: M=295 (C$_{15}$H$_{10}$ClN$_5$).

EXAMPLE 20
Using the processes described in this Application, the following compounds are obtained:
a) 4-benzylamino-5,6-dimethyl-7H-pyrrolo[2,3-d]pyrimidine hydrochloride, m.p. 115–117° C.,
b) (R)-5,6-dimethyl-4-[(1-phenyl-ethyl)-amino]-7H-pyrrolo[2,3-d]pyrimidine, m.p. 206–208° C.,
c) (S)-5,6-dimethyl-4-[(1-phenyl-ethyl)-amino]-7H-pyrrolo[2,3-d]pyrimidine, m.p. 206–207° C.,
d) (R)-6-(4-amino-phenyl)-4-[(1-phenyl-ethyl)-amino]-7H-pyrrolo[2,3-d]pyrimidine, m.p. 234–235° C., FAB-MS: (M+H)$^+$=330 (obtained by reduction of the corresponding nitro compound with Raney nickel analogously to Example 18),
e) (S)-6-(4-amino-phenyl)-4-[(1-phenyl-ethyl)-amino]-7H-pyrrolo[2,3-d]pyrimidine, m.p. 235–236° C., FAB-MS: (M+H)$^+$=330 (obtained by reduction of the corresponding nitro compound with Raney nickel analogously to Example 18),
f) 6-(4-amino-phenyl)-4-benzylamino-7H-pyrrolo[2,3-d]pyrimidine (obtained by reduction of the corresponding nitro compound with Raney nickel analogously to Example 18),
g) 6-(4-amino-phenyl)-4-[(3-chloro-benzyl)-amino]-7H-pyrrolo[2,3-d]pyrimidine (obtained by reduction of the corresponding nitro compound with Raney nickel analogously to Example 18),
h) (R)-6-(4-amino-phenyl)-4-[(1-methoxycarbonyl-benzyl)]-amino-7H-pyrrolo[2,3-d]-pyrimidine,
i) (S)-6-(4-amino-phenyl)-4-[(1-methoxycarbonyl-benzyl)]-amino-7H-pyrrolo[2,3-d]-pyrimidine,
j) 6-(4-acetylamino-phenyl)-4-(3-chloro-anilino)-7H-pyrrolo[2,3-d]pyrimidine, m.p.>310° C., MS: (M)$^+$=377,
k) 6-(4-carbamoylmethoxy-phenyl)-4-(3-chloro-anilino)-7H-pyrrolo[2,3-d]pyrimidine, m.p. 297–298° C.,
l) 6-(4-amino-phenyl)-4-(3-methyl-anilino)-7H-pyrrolo[2,3-d]pyrimidine, m.p. 288–290° C. (obtained by reduction of the corresponding nitro compound with Raney nickel analogously to Example 18),
m) 6-(4-amino-phenyl)-4-(3-chloro-4-fluoro-anilino)-7H-pyrrolo[2,3-d]pyrimidine, m.p.>300° C., MS: (M)$^+$=353 (obtained by reduction of the corresponding nitro compound with Raney nickel analogously to Example 18),
n) 6-(3-acetylamino-phenyl)-4-(3-chloro-anilino)-7H-pyrrolo[2,3-d]pyrimidine (preferably prepared analogously to Example 21), m.p.>300° C., MS: (M)$^+$=377,
o) 6-(3-amino-phenyl)-4-(3-chloro-anilino)-7H-pyrrolo[2,3-d]pyrimidine, m.p. 293–295° C. (obtained by reduction of the corresponding nitro compound with Raney nickel analogously to Example 18),
p) 6-(4-carboxymethoxy-phenyl)-4-(3-chloro-anilino)-7H-pyrrolo[2,3-d]pyrimidine, m.p. 305–307° C.,
q) 6-(4-[benzyloxycarbonyl-methoxy)-phenyl-4-(3-chloro-anilino)-7H-pyrrolo[2,3-d]-pyrimidine, m.p. 263–265° C.,
r) 6-(3-carbamoylmethoxy-phenyl)-4-(3-chloro-anilino)-7H-pyrrolo[2,3-d]pyrimidine, m.p. 283–285° C.,
s) 4-(3-chloro-anilino)-6-(4-methoxycarbonylmethoxy-phenyl)-7H-pyrroio[2,3-d]-pyrimidine, m.p. 262–264° C.,
t) 4-(3-chloro-anilino)-6-(3-methoxycarbonylmethoxy-phenyl)-7H-pyrrolo[2,3-d]-pyrimidine, m.p. 225-227° C.,
u) 6-carboxy-4-(3-chloro-anilino)-7H-pyrrolo[2,3-d]pyrimidine, m.p.>290° C., FAB-MS: (M+H)$^+$=289,
v) 4-(3-chloro-anilino)-6-ethoxycarbonyl-7H-pyrrolo[2,3-d]pyrimidine, m.p.>290° C., FAB-MS: (M+H)$^+$=317,
w) 6-n-butylaminocarbonyl-4-(3-chloro-anilino)-7H-pyrrolo[2,3-d]pyrimidine, m.p. 282–284° C., FAB-MS: (M+H)$^+$=344,
x) 4-(3-chloro-anilino)-6-(4-ethoxycarbonyl-phenyl)-7H-pyrrolo[2,3-d]pyrimidine, m.p.>300° C., FAB-MS: (M+H)$^+$=393,
y) 6-(4-carboxy-phenyl)-4-(3-chloro-anilino)-7H-pyrrolo[2, 3-d]pyrimidine, m.p.>300° C., R$_f$=0.47 (ethyl acetate/methanol [6:4]),
z) 6-benzylaminocarbonyl-4-(3-chloro-anilino)-7H-pyrrolo[2,3-d]pyrimidine, m.p. (decomp.) 295° C., FAB-MS: (M+H)$^+$=378,
za) 4-(3-chloro-anilino)-6-(N-[3-methyl-but-1-yl]-carbamoyl)-7H-pyrrolo[2,3-d]pyrimidine (cf. Example 45), m.p. 304–306° C., FAB-MS: (M+H)$^+$=358, zb) 5-(anilino-methyl)-4-(3-chloro-anilino)-7H-pyrrolo[2,3-d]pyrimidine and zc) 5-(anilino-methyl)-4-(3-chloro-anilino)-6-methyl-7H-pyrrolo[2,3-d]pyrimidine.

The above-mentioned compounds of Examples 20a, 20d, 20e, 20f, 20g, 20l and 20m are preferably obtained by reduction of the corresponding nitro compound with Raney nickel analogously to Example 18.

EXAMPLE 21

6-(4-Acetylamino-phenyl)-4-(3-chloro-anilino)-7H-pyrrolor[2,3-d]-pyrimidine (cf. Example 20j)

0.05 ml (0.56 mmol) of acetic anhydride is added to 0.2 g (0.56 mmol) of 6-(4-amino-phenyl)-4-(3-chloro-anilino)-7H-pyrrolo[2,3-d]pyrimidine suspended in 0.5 ml of pyridine, and the reaction mixture is stirred at 0° C. for 1 hour until no starting material is left in the TLC. The reaction mixture is poured into 50 ml of ice-water, and the precipitate is filtered off and washed with hexane. The crude product is chromatographed on a silica gel column. The title compound is crystallised from THF/ethyl acetate/hexane; m.p.>310° C.; MS: $(M)^+$=377.

EXAMPLE 22

The following compounds are prepared analogously to Example 1 or to the other Examples given thereafter:

a) 4-(3-chloro-anilino)-6-(4-propionylamino-phenyl)-7H-pyrrolo[2,3-d]pyrimidine (prepared analogously to Example 21); m.p.>300° C.; MS: $(M)^+$=391, b) 4-(3-chloro-anilino)-6-(3-propionylamino-phenyl)-7H-pyrrolo[2,3-d]pyrimidine (prepared analogously to Example 21); m.p.>300° C., MS: $(M)^+$=391, c) (R)-6-(4-acetylamino-phenyl)-4-[(1-phenyl-ethyl)-amino]-7H-pyrrolo[2,3-d]pyrimidine (prepared analogously to Example 21); m.p. 304-305° C.; MS: $(M)^+$=371, d) (R)-4-[(1-phenyl-ethyl)-amino]-6-(4-propionylamino-phenyl)-7H-pyrrolo[2,3-d]-pyrimidine; MS: $(M)^+$=385 (cf. Example 28a) and e) (R)-6-(3-acetylamino-phenyl)-4-[(1-phenyl-ethyl)-amino]-7H-pyrrolo[2,3-d]pyrimidine; m.p. 150–180° C.; MS: $(M)^+$=371.

EXAMPLE 23

4-(3-Chloro-anilino)-6-(4-isobutyrylamino-phenyl)-7H-pyrrolor[2,3-d]-pyrimidine 0.2 g (0.56 mmol) of 6-(4-amino-phenyl)-4-(3-chloro-anilino)-7H-pyrrolo[2,3-d]pyrimidine and 0.064 ml (0.62 mmol) of isobutyric acid chloride are stirred at 0° C. for 2 hours with 1 ml of abs. dimethylacetamide until there is no starting material left in the TLC. The reaction mixture is poured into 20 ml of ice-water and the product precipitates. The product is extracted with approximately 50 ml of ethyl acetate, approximately 2 ml of THF and 20 ml of 5% aqueous $NaHCO_3$ solution. The organic phase is washed with water, dried and concentrated by evaporation, the desired compound crystallizing out. The precipitate is filtered off and washed with cold ethyl acetate. More title compound is obtained from the mother liquor by the addition of hexane; m.p.>300° C.; MS: $(M)^+$=405.

EXAMPLE 24

The following compounds are prepared analogously to Example 23:

a) 4-(3-chloro-anilino)-6-(4-pivaloylamino-phenyl)-7H-pyrrolo[2,3)d]pyrimidine; m.p.>300° C.; MS: $(M)^+$=419, b) 4-(3-chloro-anilino)-6-[4-(DL-2-methyl-butyrylamino)-phenyl]-7H-pyrrolo[2,3-d]-pyrimidine; m.p.>300° C.; FAB-MS: $(M+H)^+$=420, c) 4-(3-chloro-anilino)-6-(4-isovalerylamino-phenyl)-7H-pyrrolo[2,3-d]pyrimidine; m.p.>300° C.; MS: $(M)^+$=419 and d) 4-(3-chloro-anilino)-6-(3-isobutyrylamino-phenyl)-7H-pyrrolo[2,3-d]pyrimidine; m.p.>300° C.; MS: $(M)^+$=405.

EXAMPLE 25

4-(3-Chloro-anilino)-6-(4-ethylamino-phenyl)-7H-pyrrolor[2,3-d]-pyrimidine

At 5° C., 110 μl (1.93 mmol) of acetaldehyde are added to 0.3 g (0.89 mmol) of 6-(4-amino-phenyl)-4-(3-chloro-anilino)-7H-pyrrolo[2,3-d]pyrimidine dissolved in 15 ml of THF and the reaction mixture is stirred at 5° C. for 24 hours (orange solution). Then 75 mg (1.15 mmol) of sodium cyanoborohydride are added. The reaction solution is stirred for a further 5 hours at room temperature and then concentrated by evaporation in vacuo. The residue is taken up in ethyl acetate and adjusted to pH 2 with 1 N HCl. The ethyl acetate phase is washed with water, dried and concentrated by evaporation. The crude product is chromatographed over a silica gel column. The title compound is crystallized from methanol/hexane or ethyl acetate/hexane; m.p. 265–270° C.; MS: $(M)^+$=363.

EXAMPLE 26

The following compounds are prepared analogously to Example 25:

a) (R)-6-(4-diethylamino-phenyl)-4-[(1-phenyl-ethyl)-amino]-7H-pyrrolo[2,3-d]pyrimidine; m.p. 286–287° C.; MS: $(M)^+$=386, b) 4-(3-chloro-anilino)-6-(4-dimethylamino-phenyl)-7H-pyrrolo[2,3-d]pyrimidine; m.p. 279–282° C.; MS: $(M)^+$=363 (formed during the reaction of 6-(4-amino-phenyl)-4-(3-chloro-anilino)-7H-pyrrolo[2,3-d]pyrimidine with formaldehyde), c) 4-(3-chloro-anilino)-6-(3-ethylamino-phenyl)-7H-pyrrolo[2,3-d]pyrimidine; MS: $(M)^+$=363 and d) 6-(4-dimethylamino-phenyl)-4-[(1-phenyl-ethyl)-amino]-7H-pyrrolo[2,3-d]pyrimidine.

EXAMPLE 27

Reduction of the corresponding nitro compound with Raney nickel analogously to Example 18 yields the following compounds:

a) 6-(4-amino-phenyl)-4-(3-methyl-benzylamino)-7H-pyrrolo[2,3-d]pyrimidine, m.p. 291–293° C.; FAB-MS: $(M+H)^+$=330, b) (R)-6-(3-amino-phenyl)-4-[(1-phenyl-ethyl)-amino]-7H-pyrrolo[2,3-d]pyrimidine, amorphous, FAB-MS: $(M+H)^+$=330, c) (R,S)-6-(4-amino-phenyl)-4-[(1-(3-chloro-phenyl)-ethyl)-amino]-7H-pyrrolo[2,3-d]-pyrimidine, m.p. 281–283° C.; FAB-MS: $(M+H)^+$=364.

EXAMPLE 28

The following compounds are prepared analogously to Example 21:

a) (R)-4-[(1-phenyl-ethyl)-amino]-6-(4-propionylamino-phenyl)-7H-pyrrolo[2,3-d]-pyrimidine, MS: $(M)^+$=385 (cf. Example 22d), b) (R)-4-[(1-phenyl-ethyl)-amino]-6-(3-propionylamino-phenyl)-7H-pyrrolo[2,3-d]-pyrimidine; MS: $(M)^+$=385.

EXAMPLE 29

The following compounds are prepared analogously to Example 23:

a) (R)-6-(3-isobutyrylamino-phenyl)-4-[(1-phenyl-ethyl)-amino]-7H-pyrrolo[2,3-d]-pyrimidine, m.p. 206–208° C.; FAB-MS: $(M+H)^+$=400, b) (R)-6-(4-isobutyrylamino-phenyl)-4-[(1-phenyl-ethyl)-amino]-7H-pyrrolo[2,3-d]-pyrimidine, m.p. 296–297° C.; FAB-MS: $(M+H)^+=400$,
c) (R)-6-(4-pivaloylamino-phenyl)-4-[(1-phenyl-ethyl)-amino]-7H-pyrrolo[2,3-d]-pyrimidine, m.p.>300° C.; FAB-MS: $(M+H)^+=414$ and
d) (R)-6-(3-pivaloylamino-phenyl)-4-[(1-phenyl-ethyl)-amino]-7H-pyrrolo[2,3-d]-pyrimidine, m.p.148–152° C.; FAB-MS: $(M+H)^+=414$.

EXAMPLE 30

4-(3-Chloro-anilino)-6-(4-ethoxycarbonyl-phenyl)-7H-pyrrolor[2,3-d]-pyrimidine 900 mg (2.95 mmol) of 4-chloro-6-(4-ethoxycarbonyl-phenyl)-7H-pyrrolo[2,3-d]-pyrimidine are heated under reflux for 2.5 hours with 0.63 ml (6 mmol) of 3-chloro-aniline and 22 ml of n-butanol. The title compound is either chromatographed on a column of silica gel or crystallized from tetrahydrofuran/diethyl ether; m.p.: >300° C.; FAB-MS: $(M+H)^+=393$.

The starting material is prepared as follows:

Step 30.1: 2-Amino-3-ethoxycarbonyl-5-(4-ethoxycarbonyl-phenyl)-1H-pyrrole

Analogously to Step 8.1, 4.92 g (29.5 mmol) of 2-amidino-acetic acid ethyl ester hydrochloride in 40 ml of absolute ethanol are reacted with 2.0 g (29.5 mmol) of sodium ethanolate and 4.0 g (14.8 mmol) of 2-bromo-(4-ethoxycarbonyl)-acetophenone to form the title compound; m.p.: 150–151° C.; MS: $(M)^+=302$.

Step 30.2: 6-(4-Ethoxycarbonyl-phenyl)-7H-Dyrrolo[2,3-d]pyrimidin-4-ol

Analogously to Step 8.2, 2.6 g (8.6 mmol) of 2-amino-3-ethoxycarbonyl-5-(4-ethoxy-carbonyl-phenyl)-1H-pyrrole are heated at 150° C. under a protective gas overnight with 19 ml of formamide, 8 ml of DMF and 0.6 ml of formic acid. Working-up analogously to Step 8.2 yields the title compound; m.p.>250° C.; FAB-MS: $(M+H)^+=284$.

Step 30.3: 4-Chloro-6-(4-ethoxycarbonyl-phenyl)-7H-pyrrolo[2,3-d]pyrimidine

Analogously to Step 8.3,1.45 g of 6-(4-ethoxycarbonyl-phenyl)-7H-pyrrolo[2,3-d]pyrimidin-4-ol in 15 ml of phosphorus oxychloride are heated under a protective gas for 2 hours and worked up, yielding the title compound; m.p.: 250° C. (decomp.): TLC-$R_f$=0.63 (ethyl acetate/hexane [1:1]); FAB-MS: $(M+H)^+=302$.

EXAMPLE 31

4-(3-Chloro-anilino)-6-(3-ethoxvcarbonyl-phenyl)-7H-pyrrolo[2,3-d]-pyrimidine

The title compound is obtained analogously to Example 30; m.p.: >300° C.; TLC-$R_f$=0.66 (ethyl acetate/hexane [1:1]); FAB-MS: $(M+H)^+=393$.

The starting material is obtained as follows:

Step 31.1: 2-Amino-3-ethoxycarbonyl-5-(3-ethoxycarbonyl-phenyl)-1H-pyrrole

The title compound is obtained analogously to Step 30.1; m.p.: 136–137° C.; TLC-$R_f$=0.37 (ethyl acetate/hexane [1:1]); MS: $(M)^+=302$.

Step 31.2: 6-(3-Ethoxycarbonyl-phenyl)-7H-pyrrolo[2,3-d]pyrimidin-4-ol

The title compound is obtained analogously to Step 30.2; m.p.: >250° C.; TLC-$R_f$=0.29 (ethyl acetate/hexane [1:1]); FAB-MS: $(M+H)^+=284$.

Step 31.3: 4-Chloro-6-(3-ethoxycarbonyl-phenyl)-7H-pyrrolo[2,3-d]pyrimidine

The title compound is obtained analogously to Step 30.3; m.p.>250° C.; TLC-$R_f$=0.62 (ethyl acetate/hexane [1:1]); FAB-MS: $(M+H)^+=302$.

EXAMPLE 32

4-(3-Chloro-anilino)-6-(4-carboxy-phenyl)-7H-pyrrolor[2,3-d]-pyrimidine (see Example 20y)

0.2 g (0.51 mmol) of 4-(3-chloro-anilino)-6-(4-ethoxycarbonyl-phenyl)-7H-pyrrolo-[2,3-d]pyrimidine, dissolved in 1.2 ml of absolute ethanol, is heated under reflux with 62.7 mg (1.52 mmol) of lithium hydroxide, dissolved in 1 ml of water, until, in the TLC, all the starting material has disappeared (12 hours). The solution is cooled to RT and adjusted to pH 2 with 1 N NaOH solution, the desired product precipitating and being filtered off. The title compound is recrystallized from ethanol/water or THF/hexane; m.p.:>300° C.; $R_f$=0.47 (ethyl acetate/methanol [60:40]), FAB-MS: $(M+H)^+=365$.

EXAMPLE 33

4-(3-Chloro-anilino)-6-(3-carboxy-phenyl)-7H-pyrrolo[2,3-d]-pyrimidine

The title compound is obtained analogously to Example 32; m.p.:>300° C.; $R_f$=0.5 (ethyl acetate/methanol [60:40]); FAB-MS: $(M+H)^+=365$.

EXAMPLE 34

4-(3-Chloro-anilino)-6-(4-methoxycarbonyl-phenyl)-7H-pyrrolo-[2,3-d]pyrimidine 0.5 g (1.37 mmol) of 4-(3-chloro-anilino)-6-(4-carboxy-phenyl)-7H-pyrrolo[2,3-d]-pyrimidine suspended in 100 ml of methanol is heated under reflux for 24 hours with 0.1 ml of concentrated sulfuric acid. The solution is concentrated and stirred in methanol/diethyl ether. The crystals are filtered off and then suspended in methanol/water. The suspension is adjusted to pH 7–8 with sodium hydrogen carbonate solution and stirred at RT for 30 min. The crystals are filtered off with suction, washed with water, methanol and diethyl ether and dried. The title compound is obtained in the form of colorless crystals, m.p.>300° C.; TLC-$R_f$=0.6 (toluene/ethyl acetate [3:7]); FAB-MS: $(M+H)^+=378$.

EXAMPLE 35

The following compounds are prepared analogously to Example 34:
a) 4-(3-chloro-anilino)-6-(4-ethoxycarbonyl-phenyl)-7H-pyrrolo[2,3-d]pyrimidine; m.p.: >300° C.; FAB-MS: $(M+H)^+=393$,
b) 4-(3-chloro-anilino)-6-(4-propyloxycarbony;-phenyl)-7H-pyrrolo[2,3-d]pyrimidine; m.p.: >250° C., $R_f$=0.41 (ethyl acetate/hexane [1:1]); FAB-MS: $(M+H)^+=407$,
c) 4-(3-chloro-anilino)-6-(4-isopropyloxycarbonyl-phenyl)-7H-pyrrolo[2,3-d]pyrimidine; m.p.: >250° C.; $R_f$=0.41 (ethyl acetate/hexane [1:1]); FAB-MS: $(M+H)^+=407$ and
d) 4-(3-chloro-anilino)-6-(4-isobutyloxycarbonyl-phenyl)-7H-pyrrolo[2,3-d]pyrimidine; m.p.: >250° C.; $R_f$=0.48 (ethyl acetate/hexane [1:1]); FAB-MS: $(M+H)^+=421$.

EXAMPLE 36

4-(3-Chloro-anilino)-6-(4-dimethylaminocarbonyl-phenyl)-7H-pyrrolor[2,3-d]pyrimidine 369 mg (1.01 mmol) of 6-(4-carboxy-phenyl)-4-(3-chloro-anilino)-7H-pyrrolo[2,3-d]-pyrimidine, 0.4 ml (2.3 mmol) of dimethylamine and 0.3 ml (1.51 mmol) of DEPC (Aldrich) in 10 ml of DMF are stirred at RT for 1 hour. The brown suspension is diluted with water and filtered and the crystals are washed with water, methanol and diethyl ether. The title compound is obtained in the form of colorless crystals, m.p.>250° C.; FAB-MS: $(M+H)^+=392$.

EXAMPLE 37
4-(3-Chloro-anilino)-6-(4-diethylaminocarbonyl-phenyl)-7H-pyrrolo[2,3-d]pyrimidine The title compound is obtained analogously to Example 8; m.p.>250° C.; FAB-MS: (M+H)$^+$=420.

EXAMPLE 38
The following compound is prepared analogously to Example 25: 4-(3-chloro-anilino)-6-(3-dimethylamino-phenyl)-7H-pyrrolo[2,3-d]pyrimidine; m.p. 282–284° C.; MS: (M)$^+$=363.

EXAMPLE 39
(R)-6-(4-Hydroxy-phenyl)-4-r(1-phenyl-ethyl)-amino]-7H-pyrrolo-[2,3-d]pyrimidine The title compound, in the form of a colorless powder, is obtained analogously to Example 10 by removing the methyl group from (R)-6-(4-methoxy-phenyl)-4-[(1-phenyl-ethyl)-amino]-7H-pyrrolo[2,3-d]pyrimidine with boron tribromide; m.p. 216–218° C.; FAB-MS: (M+H)$^+$=331.

The starting material is prepared as follows:
Step 39.1: (R)-6-(4-Methoxy-phenyl)-4-[(1-phenyl-ethyl)-amino]-7H-Dyrrolo[2,3-d]-pyrimidine The title compound is obtained analogously to Example 8 or 9 from 4-chloro-6-(4-methoxy-phenyl)-7H-pyrrolo[2,3-d]pyrimidine and (R)-(+)-1-phenyl-ethylamine in n-butanol; m.p. 256–257° C.; FAB-MS: (M+H)$^+$=345.

EXAMPLE 40
4-(3-Chloro-anilino)-5-dimethylaminomethyl-6-(4-hydroxy-phenyl)-7H-pyrrolo[2,3-d]pyrimidine The title compound is obtained analogously to Example 3 from 4-(3-chloro-anilino)-6-(4-hydroxy-phenyl)-7H-pyrrolo[2,3-d]pyrimidine and N,N-dimethyl-methyleneimmonium iodide; m.p. 243–244° C., MS: (M)$^+$=393.

EXAMPLE 41
4-(3-Chloro-anilino)-6-ethoxycarbonyl-7H-pyrrolo[2,3-d]pyrimidine Under an argon atmosphere, 29.0 g (128 mmol) of 4-chloro-6-ethoxycarbonyl-7H-pyrrolo[2,3-d]pyrimidine and 18.0 ml (171 mmol) of 3-chloro-aniline in 430 ml of n-butanol are stirred at 100° C. for 3 hours (almost dissolved after ≈1 hour, then a thick suspension forms). The reaction mixture is cooled to ~50° C., then 400 ml of isopropanol/hexane (1:1) are added thereto. The reaction mixture is then cooled to RT and the product is filtered off and washed with isopropanol and hexane. Stirring from diethyl ether yields the title compound: $^1$H-NMR (DMSO-d$_6$) 13.0 and 10.53 (2 sb, 2HN), 8.48 (s, 1H), 8.13 (m, 1H), 7.78 (dm, J=8, 1H), 7.76 (s, 1H), 7.45 (t, J=8, 1H), 7.21 (dm, J=8, 1H), 4.37 (q, J=7, 2H), 1.37 (t, J=7, 3H).

The starting material is prepared as follows:
Step 41.1: 2-Amino-3.5-bis(ethoxycarbonyl)-1H-pyrrole At 0–5° C., 56.0 g (0.43 mol) of 2-amidino-acetic acid ethyl ester [for preparation see: Liebigs Ann. Chem., 1561 (1981)] are introduced into 172 ml of DMPU. 56.0 ml (0.45 mol) of bromopyruvic acid ethyl ester are added dropwise thereto within the course of 30 min and the reaction mixture is then heated at 60° C. for 3 hours. The dark-brown reaction solution is poured into 1 liter of ice-water and extracted with 1 liter of ethyl acetate and twice with a 0.5 liter of ethyl acetate each time. The organic phases are washed three times with a 0.5 liter of water and a 0.5 liter of brine, dried (Na$_2$SO$_4$) and concentrated by evaporation. Column chromatography (SiO$_2$, hexane/ethyl acetate [1:1]) and crystallization from diethyl ether/hexane yield the title compound; m.p. 147–149° C.; MS: (M)$^+$=226.

Step 41.2: 6-Ethoxycarbonyl-4-hydroxy-7H-pyrrolo[2,3-d]pyrimidine

With the exclusion of air, 51.5 g (227 mmol) of 2-amino-3,5-bis(ethoxycarbonyl)-1H-pyrrole, 455 ml of formamide, 227 ml of DMF and 113 ml of formic acid are stirred at 140° C. for 27 hours. The resulting yellow suspension is cooled to 0–5° C. Filtering and washing with isopropanol and hexane yield the title compound; $^1$H-NMR (DMSO-d$_6$): 13–12 (2 HX), 7.99 and 7.11 (2s, 2H), 4.31 (q, J=7, 2H), 1.32 (t, J=7, 3H).

Step 41.3: 4-Chloro-6-ethoxycarbonyl-7H-pyrrolo[2,3-d]pyrimidine

Under a N$_2$ atmosphere, 32.0 g (154 mmol) of 6-ethoxycarbonyl-4-hydroxy-7H-pyrrolo[2,3-d]pyrimidine are suspended at RT in 308 ml (338 mmol) of POCl$_3$ and, with stirring, heated at 120° C., during which the solid dissolves. After 3 hours' stirring at 120° C., the excess POCl$_3$ is distilled off (65° C. external temperature; 15 mbar). The residue is suspended in 50 ml of ice-cold toluene, filtered and washed with toluene to yield the title compound; m.p. 219–221° C.; $^1$H-NMR (DMSO-d$_6$) 8.77 and 7.24 (2s, 2H), 4.39 (q, J=7, 2H), 1.36 (t, J=7, 3H). Further product can be obtained from the filtrate by concentrating by evaporation and then stirring in ethyl acetate/water.

EXAMPLE 42
6-Carboxy-4-(3-chloro-anilino)-7H-pyrrolo[2,3-d]pyrimidine

A solution of 25 mg (0.6 mmol) of LiOH.H$_2$O in 0.4 ml of H$_2$O is added dropwise to a suspension of 95 mg (0.30 mmol) of 4-(3-chloro-anilino)-6-ethoxycarbonyl-7H-pyrrolo[2,3-d]pyrimidine in 0.7 ml of methanol. The reaction mixture is heated at boiling for 4.5 hours, then cooled in an ice-bath and acidified with 0.6 ml of 1 N HCl solution. Filtering and washing with water yield the title compound; HPLC: t$_{Ret}$(Grad$_{20}$)=8.7; FAB-MS: (M+H)$^+$=289.

EXAMPLE 43
6-(N-n-Butyl-carbamoyl)-4-(3-chloro-anilino)-7H-pyrrolor[2,3-d]pyrimidine 95 mg (0.30 mmol) of 4-(3-chloro-anilino)-6-ethoxycarbonyl-7H-pyrrolo[2,3-d]pyrimidine in 1 ml of n-butylamine are heated at 60° C. for 20 hours. The pale-yellow solution is concentrated by evaporation and the residue is stirred with isopropanol, filtered and washed with hexane, yielding the title compound; m.p. 282–284° C.; TLC-R$_f$=0.45 (CH$_2$Cl$_2$/methanol 10:1); FAB-MS: (M+H)$^+$=344.

EXAMPLE 44
6-Benzylaminocarbonyl-4-(3-chloro-anilino)-7H-pVrrolof2,3-d]pyrimidine 95 mg (0.30 mmol) of 4-(3-chloro-anilino)-6-ethoxycarbonyl-7H-pyrrolo[2,3-d]pyrimidine and 0.5 ml of benzylamine are heated at 100° C. for 27 hours. The reaction mixture is cooled in ice-water, stirred with 1 ml of isopropanol and 1 ml of hexane, filtered and dried, yielding the title compound; FAB-MS: (M+H)$^+$=378.

EXAMPLE 45
4-(3-Chloro-anilino)-6-[N-(3-methyl-but-1-yl)-carbamoyl]-7H-pyrrolo[2,3-d]pyrimidine (cf. Example 20za)

95 mg (0.30 mmol) of 4-(3-chloro-anilino)-6-ethoxycarbonyl-7H-pyrrolo[2,3-d]pyrimidine in 1 ml of (3-methyl-but-1-yl)-amine are heated at 80° C. for 12 hours. The reaction mixture is concentrated by evaporation, the residue is dissolved in THF, concentrated by evaporation again, stirred with diethyl ether and filtered, yielding the title compound; m.p. 304–306° C.; FAB-MS: (M+H)$^+$=358.

EXAMPLE 46
4-(3-Chloro-anilino)-6-(N,N-dimethyl-carbamoyl)-7H-pyrrolo[2,3-d]-pyrimidine Under a $N_2$ atmosphere, 97.6 mg (0.338 mmol) of 6-carboxy-4-(3-chloro-anilino)-7H-pyrrolo[2,3-d]pyrimidine are introduced into 7 ml of DMF, and 119 mg (0.40 mmol) of TPTU and a solution of 164 mg (33% in ethanol; 1.2 mmol) of dimethylamine in 1 ml of DMF are added thereto. After 2 hours, a further 30 mg of TPTU is added to the reaction solution, which is then stirred at RT for 2 days, then poured into 30 ml of ice-water, stirred, filtered and washed with water to yield the title compound; HPLC: $t_{Ret}(Grad_{20})$=9.5; TLC-$R_f$=0.38 ($CH_2Cl_2$/methanol [10:1]); FAB-MS: $(M+H)^+$=316.

EXAMPLE 47
6-Aminocarbonyl-4-(3-chloro-anilino)-7H-pyrrolor[2,3-d]pyrimidine In an autoclave, 90 mg (0.285 mmol) of 4-(3-chloro-anilino)-6-ethoxycarbonyl-7H-pyrrolo[2,3-d]pyrimidine in 30 ml of methanol and ≈5 g of ammonia are heated at 120° C. for 48 hours. Silica gel is added to the reaction mixture, which is then concentrated by evaporation, applied in the form of a powder to a column of silica gel and, finally, eluted with methylene chloride/methanol/THF (210:35:10). Filtering with methanol through an aluminum oxide column (basic) and stirring in ethyl acetate yield the title compound; HPLC: $t_{Ret}(Grad_{20})$=8.1; TLC-$R_f$=0.18 ($CH_2Cl_2$/methanol [10:1]); high-resolution MS: $(M+H)^+$=288.0669 (calc. 288.0652).

In an alternative manner, the title compound is obtained as follows: A mixture of 2.165 g (7.5 mmol) of 6-carboxy-4-(3-chloro-anilino)-7H-pyrrolo[2,3-d]pyrimidine (cf. example 42) in 60 ml of THF and 10 ml of DMPU is refluxed for 30 min and then cooled to 0° C. (→fine suspension). Then 824 µl (7.5 mmol) of N-methylmorpholine followed by 981 µl (7.5 mmol) of isobutyl chloroformate in 10 ml of THF are added dropwise. After 1 h at 0° C., again 824 µl N-methylmorpholin and 981 µl iso-butyl chloroformate are added. The mixture is stirred for 1 h and is then added dropwise to 70 ml of a saturated solution of $NH_3$ in dioxane. After 3 h the mixture is concentrated in vacuo. The residue is poured into water, the precipitate filtered and washed with water and boiling isopropanol, yielding the title compound. More product can be isolated from the iso propanol filtrate.

EXAMPLE 48
4(3-Chloro-anilino)-6-methylaminocarbonyl-7H-pyrrolor[2,3-d]pyrimidine In a bomb tube, 95 mg (0.30 mmol) of 4-(3-chloro-anilino)-6-ethoxycarbonyl-7H-pyrrolo[2,3-d]pyrimidine in 6 ml of methylamine (33% in ethanol) are heated at 50° C. for 96 hours. The reaction mixture is concentrated by evaporation. Preparative HPLC and stirring in diethyl ether yield the title compound; HPLC: $t_{Ret}(Grad_{20})$=8.6; TLC-$R_f$=0.49 ($CH_2Cl_2$THF/ethanol [6:2:1]); FAB-MS: $(M+H)^+$=302.

EXAMPLE 49
4-(3-Chloro-anilino)-6-hydroxymethyl-7H-pyrrolor[2,3-d]pyrimidine Under a $N_2$ atmosphere, 1.4 g (37 mmol) of lithium aluminum hydride are added in portions to 5.70 g (18 mmol) of 4-(3-chloro-anilino)-6-ethoxycarbonyl-7H-pyrrolo[2,3-d]pyrimidine in 300 ml of THF. After 2 hours' stirring at 50° C., 100 ml of water are added dropwise to the reaction mixture, which is then filtered through Celite. Water is added to the filtrate, which is then extracted three times with ethyl acetate. The organic phases are washed three times with water and brine, dried ($MgSO_4$) and concentrated by evaporation. Recrystallisation from isopropanol yields the title compound; HPLC: $t_{Ret}(Grad_{20})$=8.2; TLC-$R_f$=0.11 ($CH_2Cl_2$/methanol [10:1]); MS: $(M)^+$=274.

EXAMPLE 50
4-(3-Chloro-anilino)-6-formyl-7H-pyrrolor[2,3-d]pyrimidine

With ice-cooling, 1.9 g of manganese dioxide (85%) are added to a suspension of 715 mg (2.6 mmol) of 4-(3-chloro-anilino)-6-hydroxymethyl-7H-pyrrolo[2,3-d]pyrimidine in 170 ml of methylene chloride and the reaction mixture is stirred at RT for 20 hours. Then 20 ml of DMPU are added to the reaction mixture, which is stirred for 1 hour and then filtered through Hyflo. The filtration residue is stirred again in 50 ml of methylene chloride/DMPU (1:1) (1 hour) and filtered again. The two filtrates are combined, concentrated by evaporation and taken up in ethyl acetate/THF and water. The aqueous phases are extracted twice with ethyl acetate and the organic phases are washed four times with water and brine, dried ($MgSO_4$) and concentrated by evaporation to a residual volume of ≈20 ml. The addition of diethyl ether and filtration yield the title compound; HPLC: $t_{Ret}(Grad_{20})$=10.1; TLC-$R_f$=0.24 ($CH_2Cl_2$/methanol [10:1]).

EXAMPLE 51
(R)-6-Ethoxycarbonyl-4-[1-phenyl-ethylamino]-7H-pyrrolor[2,3-d]pyrimidine Under a $N_2$ atmosphere, 902 mg (4.0 mmol) of 4-chloro-6-ethoxycarbonyl-7H-pyrrolo-[2,3-d]pyrimidine (Step 41.3) and 1.12 ml (8.8 mmol) of 1(R)-phenyl-ethylamine in 10 ml of n-butanol are stirred at 150° C. for 17 hours (initially dissolved, then thick suspension). The reaction mixture is cooled and the title compound is then filtered off and washed with isopropanol and hexane; HPLC: $t_{Ret}(Grad_{20})$=10.6; TLC-$R_f$=0.49 ($CH_2Cl_2$/methanol [10:1]); FAB-MS: $(M+H)^+$=311.

EXAMPLE 52
(R)-6-Methylaminocarbonyl-4-[1-phenyl-ethylamino]-7H-pyrrolo-[2,3-d]pyrimidine In a bomb tube, 155 mg (0.50 mmol) of 6-ethoxycarbonyl-4-[1(R)-phenyl-ethylamino]-7H-pyrrolo[2,3-d]pyrimidine and 2.5 mg (0.05 mmol) of NaCN in 4 ml of methylamine (33% in ethanol) are heated at 50° C. for 30 hours. The reaction mixture is dissolved in THF, 25 ml of water are added thereto and concentration by evaporation is carried out to a residual volume of =25 ml. The resulting crystals are filtered off and washed with water. Recrystallization from hot THF and ethyl acetate yields the title compound; HPLC: $t_{Ret}(Grad_{20})$=8.3; TLC-$R_f$=0.31 ($CH_2Cl_2$/methanol [10:1]); FAB-MS: $(M+H)^+$=296.

EXAMPLE 53
The following compounds are obtained analogously to the processes described in this text:
a) (R)-6-carbamoyl-4-[1-phenyl-ethylamino]-7H-pyrrolo[2,3-d]pyrimidine,
b) (R)-6-cyano-4-[1-phenyl-ethylamino]-7H-pyrrolo[2,3-d]pyrimidine [obtainable from compound a) above],
c) 4-(3-chloro-anilino)-6-cyano-7H-pyrrolo[2,3-d]pyrimidine [obtainable from the compound described in Example 47; cf. Example 54],
d) (R)-6-formyl-4-[1-phenyl-ethylamino]-7H-pyrrolo[2,3-d]pyrimidine,
e) (R)-6-aminomethyl-4-[1-phenyl-ethylamino]-7H-pyrrolo[2,3-d]pyrimidine [obtainable from compound d) above by reductive amination], f) 6-aminomethyl-4-(3-chloro-anilino)-7H-pyrrolo[2,3-d]pyrimidine [obtainable from the compound described in Example 50 by reductive amination], g) 4-(3-chloro-anilino)-6-(dimethylamino-methyl)-7H-pyrrolo[2,3-d]pyrimidine, h) 6-(dimethylamino-methyl)-4-[1(R)-phenyl-ethylamino]-7H-pyrrolo[2,3-d]pyrimidine, i) 6-(piperazino-methyl)-4-[1(R)-phenyl-ethylamino]-7H-pyrrolo[2,3-d]pyrimidine, and j) 4-(3-chloro-anilino)-6-(piperazino-methyl)-7H-pyrrolo[2,3-d]pyrimidine.

EXAMPLE 54

4-(3-Chloro-anilino)-6-cyano-7H-pyrrolor[2,3-d]pyrimidin (cf. Example 53c)

To 1.048 g (3.6 mmol) of 6-aminocarbonyl-4-(3-chloro-anilino)-7H-pyrrolo[2,3-d]pyrimidine (cf. example 47) and 0.7 ml of N,N-dimethyl-acetamide are added 13 ml of phosphorus oxychloride. After stirring for 1 h at room temperature and 4 h at 100° C., the reaction mixture is poured into an ice cooled saturated solution of $NaHCO_3$. Extraction with ethyl acetate (3×), washing of the organic layers with saturated $NaHCO_3$ solution, water and brine, drying ($Na_2SO_4$) and concentration results in a solid. Column chromatography ($SiO_2$; ethyl acetate) and stirring of the crude product in diethyl ether and hexane afford the title compound; m.p. 284–287° C.; TLC-$R_f$=0.71 ($CH_2Cl_2$/methanol [10:1]); HPLC: $t_{Ret}$(Grad$_{20}$)=11.8.

EXAMPLE 55

4-(3-Chloro-anilino)-6-methoxymethyl-7H-pyrrolo[2,3-d]pyrimidine

To an ice cooled suspension of 82.5 mg (0.30 mmol) of 4-(3-chloro-anilino)-6-hydroxymethyl-7H-pyrrolo[2,3-d]pyrimidin (cf. Example 49) in 5 ml of diethyl ether are added under argon 14 μl (0.15 mmol) of phosphorus tribromide. After stirring for 18 h at 0° C. and 18 h at RT (→4-(3-chloro-anilino)-6-bromomethyl-7H-pyrrolo[2,3-d]pyrimidin), 2 ml of methanol are added. The mixture is stirred for 2 h and then 1 ml of sodium methanolate (5.4 M in methanol) is added dropwise. After 18 h, the mixture is concentrated in vacuo; the residue is redissolved in methanol, silica gel is added and the mixture is evaporated to a dry powder. This powder is put on top of a chromatography column ($SiO_2$; $CH_2Cl_2$/ethanol [2:1]). Eluation with $CH_2Cl_2$/ethanol [2:1], concentration and washing with ethyl acetate/diethyl ether/hexane affords the title compound; m.p. 226–230° C.; TLC-$R_f$=0.59 ($CH_2Cl_2$/methanol [10:1]); HPLC: $t_{Ret}$(Grad$_{20}$)=9.7.

EAMPLE 56

6-(N-tert.-Butyl-carbamoyl)-4-(3-chloro-anilino)-7H-pyrrolo[2,3-d]pyrimidine

To a solution of 144 mg (0.50 mmol) of 6-carboxy-4-(3-chloro-anilino)-7H-pyrrolo[2,3-d]pyrimidine (cf. Example 42) and 116 μl (1.1 mmol) of tert.-butylamine in 5 ml of DMF are added 114 μl (0.75 mmol) of diethyl cyanophosphonate (Aldrich; Milwaukee/USA). After 4 h, the reaction mixture is poured onto ice water, stirred for 30 min and finally filtered. The residue is redissolved in isopropanol, treated with charcoal and filtered. Concentration in vacuo and washing with dichloromethane/diethyl ether yields the title compound; HPLC: $t_{Ret}$(Grad$_{20}$)=11.4; FAB-MS: (M+H)$^+$=344.

EXAMPLE 57

4-(3-Chloro-anilino)-6-(N,N-dimethylamino-methyl)-7H-pVrrolo[2,3-d]pyrimidine

A mixture of 109 mg (0.40 mmol) of 4-(3-chloro-anilino)-6-formyl-7H-pyrrolo[2,3-d]pyrimidine (cf Example 50),110 μl (0.8 mmol) of dimethylamine (33% in ethanol) and 50 μl (0.88 mmol) of acetic acid in 6 ml of methanol and 1 ml DMPU is shaken for 1 h at 50° C. Then ≈20 mg of Raney nickel are added and the mixture is hydrogenated at 50° C. The catalyst is filtered off, extensively washed with methanol and the filtrate concentrated. The residue is dissolved in ethyl acetate and saturated $NaHCO_3$ solution, the aqueous layer is separated and twice extracted with ethyl acetate. The organic phases are washed with 2× water and brine, dried ($MgSO_4$) and concentrated in vacuo. Flash chromatography ($SiO_2$; $CH_2Cl_2$/methanol [10:1→8:1]) affords the title compound; TLC-$R_f$=0.06 ($CH_2Cl_2$/methanol [10:1]); HPLC: $t_{Ret}$(Grad$_{20}$)=7.2.

EXAMPLE 58

Using the processes described in this Application, the following compounds are obtained:

a) 6-carboxy-4-(3-chloro-anilino)-5-methyl-7H-pyrrolo[2,3-d]pyrimidine, b) 4-(3-chloro-anilino)-6-formyl-5-methyl-7H-pyrrolo[2,3-d]pyrimidine, c) 4-(3-chloro-anilino)-6-hydroxymethyl-5-methyl-7H-pyrrolo[2,3-d]pyrimidine, d) 5-carboxy-4-(3-chloro-anilino)-6-methyl-7H-pyrrolo[2,3-d]pyrimidine, e) 4-(3-chloro-anilino)-5-formyl-6-methyl-7H-pyrrolo[2,3-d]pyrimidine, and f) 4-(3-chloro-anilino)-5-hydroxymethyl-6-methyl-7H-pyrrolo[2,3-d]pyrimidine.

EXAMPLE 59

Dry-filled capsules 5000 capsules, each comprising as active ingredient 0.25 g of one of the compounds of formula I mentioned in the preceding Examples, are prepared as follows:

| Composition | |
| --- | --- |
| active ingredient | 1250 g |
| talcum | 180 g |
| wheat starch | 120 g |
| magnesium stearate | 80 g |
| lactose | 20 g |

Preparation process: The mentioned substances are pulverized and forced through a sieve of 0.6 mm mesh size. 0.33 g portions of the mixture are introduced into gelatin capsules using a capsule-filling machine.

EXAMPLE 60

Soft capsules 5000 soft gelatin capsules, each comprising as active ingredient 0.05 g of one of the compounds of formula I mentioned in the preceding Examples, are prepared as follows:

| Composition | |
| --- | --- |
| active ingredient | 250 g |
| Lauroglycol | 2 liters |

Preparation process: The active ingredient is pulverized and suspended in Lauroglycol® (propylene glycol laurate, Gattefossé S.A., Saint Priest, France) and ground in a wet pulverizer to a particle size of approx. from 1 to 3 µm. 0.419 g portions of the mixture are then introduced into soft gelatin capsules using a capsule-filling machine.

EXAMPLE 61

Soft capsules 5000 soft gelatin capsules, each comprising as active ingredient 0.05 g of one of the compounds of formula I mentioned in the preceding Examples, are prepared as follows:

| Composition | |
| --- | --- |
| active ingredient | 250 g |
| PEG 400 | 1 liter |
| Tween 80 | 1 liter |

Preparation process: The active ingredient is pulverized and suspended in PEG 400 (polyethylene glycol having an M, of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulverizer to a particle size of approx. from 1 to 3 µm. 0.43 g portions of the mixture are then introduced into soft gelatin capsules using a capsule-filling machine.

What is claimed is:

1. A 7H-pyrrolo[2,3-d]pyrimidine derivative of formula I

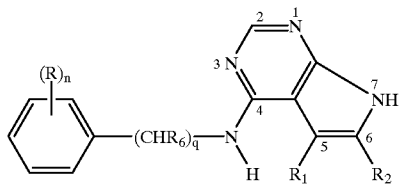

(I)

wherein q is 0 or 1, n is from 1 to 3 when q is 0, or n is from 0 to 3 when q is 1, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other α) phenyl substituted by carbamoylmethoxy, carboxymethoxy, benzyloxycarbonylmethoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro;

β) hydrogen, with the proviso that $R_1$ and $R_2$ are not hydrogen simultaneously;

γ) unsubstituted or halo- or lower alkyl-substituted pyridyl;

δ) N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzylcarbamoyl; formyl; lower alkanoyl; lower alkenyl; lower alkenyloxy; or ε) lower alkyl substituted by εα) halogen, amino, lower alkylamino, piperazino, di-lower alkylamino, εβ) phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by tyrifluoromethyl, εγ) hydroxy, lower alkoxy, cyano, carboxy, lower alkoxycarbonyl, carbamoyl, N-lower alkyl-carbamoyl, N,N-di-lower alkyl-carbamoyl, mercapto or εδ) a radical of the formula $R_3$—$S(O)_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) when q is 1, $R_1$ and $R_2$ are each independently of the other unsubstituted lower alkyl with the exception of methyl or unsubstituted phenyl or have one of the meanings given above in paragraph a), and $R_6$ is hydrogen, lower alkyl, lower alkoxycarbonyl, carbamoyl, N-lower alkyl-carbamoyl or N,N-di-lower alkyl-carbamoyl, or a salt thereof, with the exception of the compound of formula I wherein n is 0, q is 1, $R_1$ and $R_6$ are each hydrogen and $R_2$ is methyl, the compound of formula I wherein n is 2, q is 1, $R_1$ and $R_6$ are each hydrogen, $R_2$ is methyl and R is 3,4-methoxy and the compounds of formula I wherein n is 1, q is 0, $R_1$ is 3-pyridyl, 4-cyanophenyl or 4-hydroxyphenyl, $R_2$ is hydrogen and R is fluoro.

2. A compound of formula I according to claim 1 wherein q is 0 or 1, n is from 1 to 3 when q is 0, or n is from 0 to 3 when q is 1, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ is hydrogen and $R_2$ is phenyl substituted by carbamoylmethoxy, carboxy-methoxy, benzyloxycarbonyl-methoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen; phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl; lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) when q is 1, $R_1$ is hydrogen and $R_2$ is unsubstituted phenyl, and $R_6$ is hydrogen, lower alkyl, lower alkoxycarbonyl, carbamoyl, N-lower alkyl-carbamoyl or N,N-di-lower alkyl-carbamoyl, or a salt thereof.

3. A compound of formula I according to claim 1 wherein
q is 0 or 1,
n is from 1 to 3 when q is 0, or n is from 0 to 3 when q is 1,
R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different a) $R_1$ and $R_2$ are each independently of the other phenyl substituted by carbamoylmethoxy, carboxy-methoxy, benzyloxycarbonyl-methoxy, lower alkoxycarbonylmethoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen, with the proviso that $R_1$ and $R_2$ are not hydrogen simultaneously; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyno, carboxy, lower alkoxycarbonyl, carbamoyl, N-lower alkyl-carbamoyl, N,N-di-lower alkylcarbamoyl, mercapto or by a radical of the formula $R_3$—$S(O)_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c) when q is 1, $R_1$ and $R_2$ are each independently of the other unsubstituted lower alkyl with the exception of methyl or unsubstituted phenyl or have one of the meanings given above in paragraph a) and $R_6$ is hydrogen, lower alkyl, lower alkoxycarbonyl, carbamoyl, N-lower alkyl-carbamoyl or N,N-di-lower alkyl-carbamoyl, or a salt thereof,
with the exception of the compound of formula I wherein n is 0, q is 1, $R_1$ and $R_6$ are each hydrogen and $R_2$ is methyl, the compound of formula I wherein n is 2, q is 1, $R_1$ and $R_6$ are each hydrogen, $R_2$ is methyl and R is 3,4-methoxy and the compounds of formula I wherein n is 1, q is 0, $R_1$ is 3-pyridyl, 4-cyanophenyl or 4-hydroxyphenyl, $R_2$ is hydrogen and R is fluoro.

4. A compound of formula I according to claim 1 wherein
q is 0,
n is from 1 to 3,
R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen, with the proviso that $R_1$ and $R_2$ are not hydrogen simultaneously; unsubstituted or halo- or lower alkyl-substituted pyridyl; N-benzyl-pyridinium-2-yl; naphthyl; cyano; carboxy; lower alkoxycarbonyl; carbamoyl; N-lower alkyl-carbamoyl; N,N-di-lower alkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or a salt thereof,
with the exception of the compounds of formula I wherein n is 1, q is 0, $R_1$ is 3-pyridyl, 4-cyanophenyl or 4-hydroxyphenyl, $R_2$ is hydrogen and R is fluoro.

5. A compound of formula I according to claim 1 wherein
q is 0,
n is 1 or 2,
R is halogen, it being possible when [several] two radicals R are present in the molecule for those radicals to be identical or different, and a) $R_1$ and $R_2$ are each independently of the other phenyl substituted by phenyl, amino, hydroxy or by nitro; hydrogen, with the proviso that $R_1$ and $R_2$ are not hydrogen simultaneously; pyridyl; N-benzylpyridinium-2-yl; naphthyl; or lower alkyl substituted by di-lower alkylamino, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or a salt thereof,
with the exception of the compounds of formula I wherein n is 1, q is 0, R is 3-pyridyl or 4-hydroxyphenyl, $R_2$ is hydrogen and R is fluoro.

6. A compound of formula I according to claim 1 wherein
q is 0,
n is 1 or 2,
R is halogen, it being possible when two radicals R are present in the molecule for those radicals to be identical or different, and
a) $R_1$ is hydrogen, or lower alkyl that is unsubstituted or substituted by di-lower alkyl-amino, and $R_2$ is phenyl substituted by phenyl, amino, hydroxy or by nitro; pyridyl; N-benzyl-pyridinium-2-yl; or naphthyl,
or a salt thereof.

7. A compound of formula I according to claim 1 wherein
q is 0 or 1,
n is 1 or 2 when q is 0, or n is from 0 to 2 when q is 1,
R is halogen or lower alkyl, it being possible when two radicals R are present in the molecule for those radicals to be identical or different, and
$R_1$ is hydrogen, or lower alkyl that is unsubstituted or substituted by di-lower alkyl-amino, and $R_2$ is phenyl substituted by carbamoylmethoxy, carboxymethoxy, benzyl-oxycarbonylmethoxy, lower alkoxycarbonylmethoxy, lower alkoxycarbonyl, carboxy, N,N-di-lower alkyl-carbamoyl, phenyl, amino, lower alkylamino, di-lower alkylamino, lower alkanoylamino, hydroxy or by nitro; hydroxy-lower alkyl, amino-lower alkyl, di-lower alkylamino-lower alkyl, piperazino-lower alkyl, formyl, cyano, carboxy; lower alkoxycarbonyl; carbamoyl, N-lower alkyl-carbamoyl; N,N-di-lower alkyl-carbamoyl, pyridyl; N-benzyl-carbamoyl, N-benzyl-pyridinium-2-yl; or naphthyl;
$R_6$ is hydrogen, methyl or lower alkoxycarbonyl,
or a pharmaceutically acceptable salt thereof.

8. A compound of formula I according to claim 1 wherein
q is 0 or 1,
n is 1 or 2 when q is 0, or n is from 0 to 2 when q is 1,
R is halogen, it being possible when two radicals R are present in the molecule for those radicals to be identical or different, and
$R_1$ is hydrogen, or lower alkyl that is unsubstituted or substituted by di-lower alkylamino, and $R_2$ is phenyl substituted by carbamoylmethoxy, carboxymethoxy, benzyloxycarbonylmethoxy, methoxycarbonylmethoxy, ethoxycarbonyl, carboxy, phenyl, amino, acetamino, hydroxy or by nitro; carboxy; ethoxycarbonyl; N-lower alkyl-carbamoyl; pyridyl; N-benzyl-pyridinium-2-yl; or naphthyl;
$R_6$ is hydrogen, methyl or methoxycarbonyl,
or a salt thereof.

9. A compound of formula I according to claim 1 selected from
4-(3-chloro-anilino)-6-(pyrid-2-yl)-7H-pyrrolo[2,3-d]pyrimidine,
4-(3-chloro-anilino)-6-(pyrid-2-yl)-7H-pyrrolo[2,3-d]pyrimidine hydrochloride,
4-(3-chloro-anilino)-5-dimethylaminomethyl-6-(pyrid-2-yl)-7H-pyrrolo[2,3-d]pyrimidine,
4-(3-chloro-4-fluoro-anilino)-6-(pyrid-2-yl)-7H-pyrrolo[2,3-d]pyrimidine,
4-(3-chloro-anilino)-5-methyl-6-(pyrid-2-yl)-7H-pyrrolo[2,3-d]pyrimidine,
4-(3-chloro-anilino)-5-methyl-6-(N-benzyl-pyridinium-2-yl)-7H-pyrrolo[2,3-d]pyrimidine bromide,
4-(3-chloro-4-fluoro-anilino)-5-methyl-6-(pyrid-2-yl)-7H-pyrrolo[2,3-d]pyrimidine,
4-(3-chloro-anilino)-6-(biphen-4-yl)-7H-pyrrolo[2,3-d]pyrimidine,
4-(3-chloro-anilino)-6-(naphth-2-yl)-7H-pyrrolo[2,3-d]pyrimidine,
4-(3-chloro-anilino)-6-(2-hydroxy-phenyl)-7H-pyrrolo[2,3-d]pyrimidine hydrobromide,
4-(3-chloro-anilino)-6-(3-hydroxy-phenyl)-7H-pyrrolo[2,3-d]pyrimidine hydrobromide,
4-(3-chloro-anilino)-6-(4-hydroxy-phenyl)-7H-pyrrolo[2,3-d]pyrimidine hydrobromide,
4-(3-chloro-anilino)-5-dimethylaminomethyl-6-(4-hydroxy-phenyl)-7H-pyrrolo[2,3-d]-pyrimidine,
4-(3-chloro-anilino)-5-dimethylaminomethyl-6-phenyl-7H-pyrrolo[2,3-d]pyrimidine,
4-(3-chloro-anilino)-5-methyl-6-(4-hydroxy-phenyl)-7H-pyrrolo[2,3-d]pyrimidine hydrobromide,
4-(3-chloro-anilino)-6-(4-nitro-phenyl)-7H-pyrrolo[2,3-d]pyrimidine and
4-(3-chloro-anilino)-6-(4-amino-phenyl)-7H-pyrrolo[2,3-d]pyrimidine
or a pharmaceutically acceptable salt.

10. A compound of formula I according to claim 1 selected from
a) (R)-6-(4-amino-phenyl)-4-[(1-phenyl-ethyl)-amino]-7H-pyrrolo[2,3-d]pyrimidine,
b) (S)-6-(4-amino-phenyl)-4-[(1-phenyl-ethyl)-amino]-7H-pyrrolo[2,3-d]pyrimidine,
c) 6-(4-amino-phenyl)-4-benzylamino-7H-pyrrolo[2,3-d]pyrimidine,
d) 6-(4-amino-phenyl)-4-[(3-chloro-benzyl)-amino]-7H-pyrrolo[2,3-d]pyrimidine,
e) (R)-6-(4-amino-phenyl)-4-[(1-methoxycarbonyl-benzyl)]-amino-7H-pyrrolo[2,3-d]-pyrimidine,
f) (S)-6-(4-amino-phenyl)-4-[(1-methoxycarbonyl-benzyl)]-amino-7H-pyrrolo[2,3-d]-pyrimidine,
g) 6-(4-acetylamino-phenyl)-4-(3-chloro-anilino)-7H-pyrrolo[2,3-d]pyrimidine,
h) 6-(4-carbamoylmethoxy-phenyl)-4-(3-chloro-anilino)-7H-pyrrolo[2,3-d]pyrimidine,
i) 6-(4-amino-phenyl)-4-(3-methyl-anilino)-7H-pyrrolo[2,3-d]pyrimidine,
j) 6-(4-amino-phenyl)-4-(3-chloro-4-fluoro-anilino)-7H-pyrrolo[2,3-d]pyrimidine,
k) 6-(3-acetylamino-phenyl)-4-(3-chloro-anilino)-7H-pyrrolo[2,3-d]pyrimidine,
l) 6-(3-amino-phenyl)-4-(3-chloro-anilino)-7H-pyrrolo[2,3-d]pyrimidine,
m) 6-(4-carboxymethoxy-phenyl)-4-(3-chloro-anilino)-7H-pyrrolo[2,3-d]pyrimidine,
n) 6-(4-[benzyloxycarbonyl-methoxy]-phenyl)-4-(3-chloro-anilino)-7H-pyrrolo[2,3-d]-pyrimidine,
o) 6-(3-carbamoylmethoxy-phenyl)-4-(3-chloro-anilino)-7H-pyrrolo[2,3-d]pyrimidine,
p) 4-(3-chloro-anilino)-6-(4-methoxycarbonyimethoxy-phenyl)-7H-pyrrolo[2,3-d]-pyrimidine,
q) 4-(3-chloro-anilino)-6-(3-methoxycarbonyl methoxy-phenyl)-7H-pyrrolo[2,3-d]-pyrimidine,
r) 6-carboxy-4-(3-chloro-anilino)-7H-pyrrolo[2,3-d]pyrimidine,
s) 4-(3-chloro-anilino)-6-ethoxycarbonyl-7H-pyrrolo[2,3-d]pyrimidine,
t) 6-(N-n-butyl-carbamoyl)-4-(3-chloro-anilino)-7H-pyrrolo[2,3-d]pyrimidine,
u) 4-(3-chloro-anilino)-6-(4-ethoxycarbonyi-phenyl)-7H-pyrrolo[2,3-d]pyrimidine,
v) 6-(4-carboxy-phenyl)-4-(3-chloro-anilino)-7H-pyrroio[2,3-d]pyrimidine, x) 6-(N-benzyl-carbamoyl)-4-(3-chloro-anilino)-7H-pyrrolo[2,3-d]pyrimidine and
za) 4-(3-chloro-anilino)-6-(N-[3-methyl-but-1-yl]-carbamoyl)-7H-pyrrolo[2,3-d]pyrimidine
or a pharmaceutically acceptable salts thereof.

11. A compound of formula I according to claim 1 selected from
a) 4-(3-chloro-anilino)-6-(4-propionylamino-phenyl)-7H-pyrrolo[2,3-d]pyrimidine,
b) 4-(3-chloro-anilino)-6-(3-propionylamino-phenyl)-7H-pyrrolo[2,3-d]pyrimidine,
c) (R)-6-(4-acetylamino-phenyl)-4-[(1-phenyl-ethyl)-amino]-7H-pyrrolo[2,3-d]pyrimidine,
d) (R)-4-[(1-phenyl-ethyl)-amino]-6-(4-propionylamino-phenyl)-7H-pyrrolo[2,3-d]-pyrimidine,
e) (R)-6-(3-acetylamino-phenyl)-4-[(1-phenyl-ethyl)-amino]-7H-pyrrolo[2,3-d]pyrimidine,
f) 4-(3-chloro-anilino)-6-(4-isobutyrylamino-phenyl)-7H-pyrrolo[2,3-d]pyrimidine,
g) 4-(3-chloro-anilino)-6-(4-pivaloylamino-phenyl)-7H-pyrrolo[2,3-d]pyrimidine,
h) 4-(3-chloro-anilino)-6-[4-(DL-2-methyl-butyrylamino)-phenyl]-7H-pyrrolo[2,3-d]-pyrimidine,
i) 4-(3-chloro-anilino)-6-(4-isovalerylamino-phenyl)-7H-pyrrolo[2,3-d]pyrimidine,
j) 4-(3-chloro-anilino)-6-(3-isobutyrylamino-phenyl)-7H-pyrrolo[2,3-d]pyrimidine,
k) 4-(3-chloro-anilino)-6-(4-ethylamino-phenyl)-7H-pyrrolo[2,3-d]pyrimidine,
l) (R)-6-(4-diethylamino-phenyl)-4-[(1-phenyl-ethyl)-amino]-7H-pyrrolo[2,3-d]pyrimidine,
m) 4-(3-chloro-anilino)-6-(4-dimethylamino-phenyl)-7H-pyrrolo[2,3-d]pyrimidine,
n) 4-(3-chloro-anilino)-6-(3-ethylamino-phenyl)-7H-pyrrolo[2,3-d]pyrimidine and
o) 6-(4-dimethylamino-phenyl)-4-[(1-phenyl-ethyl)-amino]-7H-pyrrolo[2,3-d]pyrimidine
or a pharmaceutically acceptable salts thereof.

12. A compound of formula I according to claim 1 selected from
6-(4-amino-phenyl)-4-(3-methyl-benzylamino)-7H-pyrrolo[2,3-d]pyrimidine,
(R)-6-(3-amino-phenyl)-4-[(1-phenyl-ethyl)-amino]-7H-pyrrolo[2,3-d]pyrimidine,
(R,S)-6-(4-amino-phenyl)-4-[(1-(3-chloro-phenyl)-ethyl)-amino]-7H-pyrrolo[2,3-d]-pyrimidine,
(R)-4-[(1-phenyl-ethyl)-amino]-6-(4-propionylamino-phenyl)-7H-pyrrolo[2,3-d]-pyrimidine,
(R)-4-[(1-phenyl-ethyl)-amino]-6-(3-propionylamino-phenyl)-7H-pyrrolo[2,3-d]-pyrimidine,
(R)-6-(3-isobutyrylamino-phenyl)-4-[(1-phenyl-ethyl)-amino]-7H-pyrrolo[2,3-d]-pyrimidine,
(R)-6-(4-isobutyrylamino-phenyl)-4-[(1-phenyl-ethyl)-amino]-7H-pyrrolo[2,3-d]-pyrimidine,
(R)-6-(4-pivaloylamino-phenyl)-4-[(1-phenyl-ethyl)-amino]-7H-pyrrolo[2,3-d]pyrimidine,
(R)-6-(3-pivaloylamino-phenyl)-4-[(1-phenyl-ethyl)-amino]-7H-pyrrolo[2,3-d]pyrimidine,
4-(3-chloro-anilino)-6-(3-ethoxycarbonyl-phenyl)-7H-pyrrolo[2,3-d]pyrimidine,
4-(3-chloro-anilino)-6-(3-carboxy-phenyl)-7H-pyrrolo[2,3-d]pyrimidine,
4-(3-chloro-anilino)-6-(4-methoxycarbonyl-phenyl)-7H-pyrrolo[2,3-d]pyrimidine,
4-(3-chloro-anilino)-6-(4-propyloxycarbonyl-phenyl)-7H-pyrrolo[2,3-d]pyrimidine,
4-(3-chloro-anilino)-6-(4-isopropyloxycarbonyi-phenyl)-7H-pyrrolo[2,3-d]pyrimidine,
4-(3-chloro-anilino)-6-(4-isobutyloxycarbonyl-phenyl)-7H-pyrrolo[2,3-d]pyrimidine,
4-(3-chloro-anilino)-6-(4-dimethylaminocarbonyl-phenyl)-7H-pyrrolo[2,3-d]pyrimidine,
4-(3-chloro-anilino)-6-(4-diethylaminocarbonyl-phenyl)-7H-pyrrolo[2,3-d]pyrimidine,
(R)-6-(4-diethylamino-phenyl)-4-[(1-phenyl-ethyl)-amino]-7H-pyrrolo[2,3-d]pyrimidine,
4-(3-chloro-anilino)-6-(3-dimethylamino-phenyl)-7H-pyrrolo[2,3-d]pyrimidine,
4-(3-chloro-anilino)-5-dimethylaminomethyl-6-(4-hydroxy-phenyl)-7H-pyrrolo[2,3-d]-pyrimidine,
4-(3-chloro-anilino)-6-(N,N-dimethyl-carbamoyl)-7H-pyrrolo[2,3-d]pyrimidine,
6-aminocarbonyl-4-(3-chloro-anilino)-7H-pyrrolo[2,3-d]pyrimidine,
4-(3-chloro-anilino)-6-methylaminocarbonyl-7H-pyrrolo[2,3-d]pyrimidine,
4-(3-chloro-anilino)-6-hydroxymethyl-7H-pyrrolo[2,3-d]pyrimidine,
4-(3-chloro-anilino)-6-formyl-7H-pyrrolo[2,3-d]pyrimidine,
(R)-6-ethoxycarbonyl-4-[1-phenyl-ethylamino]-7H-pyrrolo[2,3-d]pyrimidine,
(R)-6-methylaminocarbonyl-4-[1-phenyl-ethylamino]-7H-pyrrolo[2,3-d]pyrimidine,
(R)-6-carbamoyl-4-[1-phenyl-ethylamino]-7H-pyrrolo[2,3-d]pyrimidine,
(R)-6-cyano-4-[1-phenyl-ethylamino]-7H-pyrrolo[2,3-d]pyrimidine,
4-(3-chloro-anilino)-6-cyano-7H-pyrrolo[2,3-d]pyrimidine,
(R)-6-formyl-4-[1-phenyl-ethylamino]-7H-pyrrolo[2,3-d]pyrimidine,
(R)-6-aminomethyl-4-[1-phenyl-ethylamino]-7H-pyrrolo[2,3-d]pyrimidine,
6-aminomethyl-4-(3-chloro-anilino)-7H-pyrrolo[2,3-d]pyrimidine,
4-(3-chloro-anilino)-6-(dimethylamino-methyl)-7H-pyrrolo[2,3-d]pyrimidine,
(R)-6-(dimethylamino-methyl)-4-[1-phenyl-ethylamino]-7H-pyrrolo[2,3-d]pyrimidine,
(R)-6-(piperazino-methyl)-4-[1-phenyl-ethylamino]-7H-pyrrolo[2,3-d]pyrimidine,
4-(3-chloro-anilino)-6-(piperazino-methyl)-7H-pyrrolo[2,3-d]pyrimidine,
4-(3-chloro-anilino)-6-methoxymethyl-7H-pyrrolo[2,3-d]pyrimidine,
6-(N-tert.-Butyl-carbamoyl)-4-(3-chloro-anilino)-7H-pyrrolo[2,3-d]pyrimidine,
4-(3-chloro-anilino)-6-(N,N-dimethylamino-methyl)-7H-pyrrolo[2,3-d]pyrimidine,
6-carboxy-4-(3-chloro-anilino)-5-methyl-7H-pyrrolo[2,3-d]pyrimidine,
4-(3-chloro-anilino)-6-formyl-5-methyl-7H-pyrrolo[2,3-d]pyrimidine,
4-(3-chloro-anilino)-6-hydroxymethyl-5-methyl-7H-pyrrolo[2,3-d]pyrimidine,
5-carboxy-4-(3-chloro-anilino)-6-methyl-7H-pyrrolo[2,3-d]pyrimidine,
4-(3-chloro-anilino)-5-formyl-6-methyl-7H-pyrrolo[2,3-d]pyrimidine, and
4-(3-chloro-anilino)-5-hydroxymethyl-6-methyl-7H-pyrrolo[2,3-d]pyrimidine,
or a pharmaceutically acceptable salt thereof.

13. A compound of formula I according to claim 1 wherein
q is 0 or 1, n is from 1 to 3 when q is 0, or n is from 0 to 3 when q is 1, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different.

$R_1$ is hydrogen, or lower alkyl that is unsubstituted or substituted by di-lower alkylamino, and $R_2$ is phenyl substituted by carbamoylmethoxy, carboxymethoxy, benzyloxycarbonylmethoxy, lower alkoxycarbonylmethoxy, lower alkoxycarbonyl, carboxy, N,N-di-lower alkyl-carbamoyl, phenyl, amino, lower alkylamino, di-lower alkylamino, lower alkanoylamino, hydroxy or by nitro;

$R_6$ is hydrogen, lower alkyl, lower alkoxycarbonyl, carbamoyl, N-lower alkyl-carbamoyl or N,N-di-lower alkyl-carbamoyl, or a salt thereof.

14. A compound of formula I according to claim 1 wherein q is 1.

15. A compound of formula I according to claim 2 wherein q is 1.

16. A compound of formula I according to claim 3 wherein q is 1.

17. A compound of formula I according to claim 7 wherein q is 1.

18. A compound of formula I according to claim 8 wherein q is 1.

19. A compound of formula I according to claim 13 wherein q is 1.

20. A compound of formula I according to claim 1 which is (R)-6-(4-hydroxy-phenyl)-4-[(1-phenyl-ethyl)-amino]-7H-pyrrolo[2,3-d]pyrimidine, or a pharmaceutically acceptable salt thereof.

21. A process for the preparation of a 7H-pyrrolo[2,3-d] pyrimidine derivative of formula I

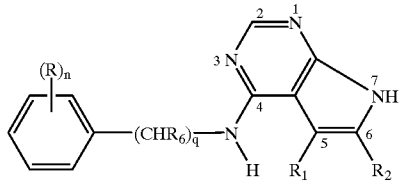

(I)

wherein q is 0 or 1, n is from 1 to 3 when q is 0, or n is from 0 to 3 when q is 1, R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other α) phenyl substituted by carbamoylmethoxy, carboxymethoxy, benzyloxycarbonylmethoxy, lower alkoxycarbonyl-methoxy, phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro;

β) hydrogen, with the proviso that $R_1$ and $R_2$ are not hydrogen simultaneously;

γ) unsubstituted or halo- or lower alkyl-substituted pyridyl;

δ) N-benzyl-pyridinium-2-yl; naphthyl; cyano; carboxy; lower alkoxycarbonyl; carbamoyl; N-lower alkyl-carbamoyl; N,N-di-lower alkyl-carbamoyl; N-benzylcarbamoyl; formyl; lower alkanoyl; lower alkenyl; lower alkenyloxy; or ε) lower alkyl substituted by εα) halogen, amino, lower alkylamino, piperazino, di-lower alkylamino, εβ) phenylamino that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or by trifluoromethyl, εγ) hydroxy, lower alkoxy, cyano, carboxy, lower alkoxycarbonyl, carbamoyl, N-lower alkyl-carbamoyl, N,N-di-lower alkyl-carbamoyl, mercapto or εδ) a radical of the formula $R_3$—S(O)$_m$— wherein $R_3$ is lower alkyl and m is 0, 1 or 2, or b) when q is 0, one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or c when q is 1, $R_1$ and $R_2$ are each independently of the other unsubstituted lower alkyl with the exception of methyl or unsubstituted phenyl or have one of the meanings given above in paragraph a), and $R_6$ is hydrogen, lower alkyl, lower alkoxycarbonyl, carbamoyl, N-lower alkyl-carbamoyl or N,N-di-lower alkyl-carbamoyl, or a salt thereof, with the exception of the compound of formula I wherein n is 0, 1 is 1, $R_1$ and $R_6$ are each hydrogen and $R_2$ is methyl, the compound of formula I wherein n is 2, q is 1, $R_1$ and R6 are each hydrogen, $R_2$ is methyl and R is 3,4-methoxy and the compounds of formula I wherein n is 1, q is 0, $R_1$ is 3-pyridyl, 4-cyanophenyl or 4-hydroxyphenyl, $R_2$ is hydrogen and R is fluoro, which process comprises a) reacting a pyrrolo[2,3-d]pyrimidine derivative of formula II

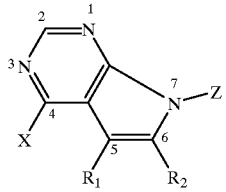

(II)

wherein X is a suitable leaving group, Z is hydrogen or 1-aryl-lower alkyl and the remaining substituents are as defined above for compounds of formula I, any free functional groups present in the radicals $R_1$ and $R_2$ being protected if necessary by readily removable protecting groups, with an amine of formula III

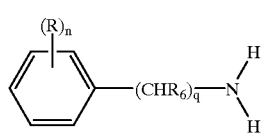

(III)

wherein R, $R_6$, n and q are as defined above for compounds of formula I, any free functional groups present in the radical R being protected if necessary by readily removable protecting groups, and removing any protecting groups that are present and, where it is present, the 1-aryl-lower alkyl radical Z, and if necessary for the preparation of a salt, converting a resulting free compound of formula I into a salt or, if necessary for the preparation of a free compound, converting a resultant salt of a compound of formula I into the free compound.

22. A process for the preparation of a 7H-pyrrolo[2,3-d] pyrimidine derivative of formula Ia

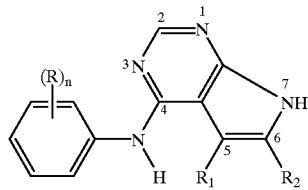

(Ia)

wherein n is from 1 to 3,

R is halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amino, lower alkanoylamino, lower alkylamino, N,N-di-lower alkylamino or trifluoromethyl, it being possible when several radicals R are present in the molecule for those radicals to be identical or different, a) $R_1$ and $R_2$ are each independently of the other phenyl substituted by phenyl, amino, lower alkanoylamino, lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano or by nitro; hydrogen, with the proviso that $R_1$ and $R_2$ are not hydrogen simultaneously; unsubstituted or halo- or lower alkyl-substituted pyridyl; N-benzyl-pyridimium-2-yl; naphthyl; cyano; carboxy; lower alkoxycarbonyl; carbamoyl; N-lower alkyl-carbamoyl; N,N-diloweralkyl-carbamoyl; formyl; lower alkanoyl; lower alkenyl; lower alkenyloxy; or lower alkyl substituted by halogen, amino, lower alkylamino, piperazino, di-lower alkylamino, hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_3$—$S(O)_m$— wherein $R_3$ is lower alkyl and m is 0, 1 or 2, or b) one of the radicals $R_1$ and $R_2$ is unsubstituted lower alkyl or unsubstituted phenyl and the other of the radicals $R_1$ and $R_2$ has one of the meanings given above in paragraph a) with the exception of hydrogen, or a salt thereof, with the exception of the compounds of formula I wherein n is 1, q is 0, $R_1$ is 3-pyridyl, 4-cyanophenyl or 4-hydroxyphenyl, $R_2$ is hydrogen and R is fluoro, which comprises a) reacting a pyrrolo[2,3-d]pyrimidine derivative of formula II

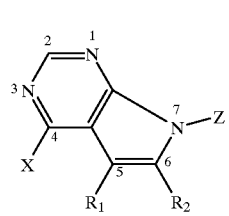

(II)

wherein X is a suitable leaving group, Z is hydrogen or 1-aryl-lower alkyl and the remaining substituents are as defined above for compounds of formula Ia, any free functional groups present in the radicals $R_1$ and $R_2$ being protected if necessary by readily removable protecting groups, with an aniline derivative of formula IIIa

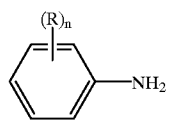

(IIIa)

wherein R and n are as defined above for compounds of formula Ia, any free functional groups present in the radical R being protected if necessary by readily removable protecting groups, and removing any protecting groups that are present and, where it is present, the 1-aryl-lower alkyl radical Z, and, if necessary for the preparation of a salt, converting a resulting free compound of formula Ia into a salt or, if necessary for the preparation of a free compound, converting a resulting salt of a compound of formula Ia into the free compound.

23. A pharmaceutical composition comprising a pharmaceutically acceptable carrier or diluent and a therapeutically effective amount of a compound of formula I according to claim 1, or a pharmaceutically acceptable salt thereof.

24. A method of inhibiting protein tyrosine kinases in a warm-blooded animal comprising administering to said warm-blooded animal a therapeutically effective amount of a compound of formula I according to claim 1, or a pharmaceutically acceptable salt thereof.

25. A method of treating tumors mediated by protein tyrosine kinase inhibition comprising administering to said warm-blooded animal a therapeutically effective amount of a compound of formula I according to claim 1, or a pharmaceutically acceptable salt thereof.

* * * * *

UNITED STATES PATENT AND TRADEMARK OFFICE
CERTIFICATE OF CORRECTION

PATENT NO. : 6,140,332
DATED : October 31, 2000
INVENTOR(S) : Traxler et al.

It is certified that error appears in the above-identified patent and that said Letters Patent is hereby corrected as shown below:

Title page,
Item [57], ABSTRACT,
Lines 1 and 4, respectively, beneath the structural formula should read:
-- wherein the substituents are as defined in claim 1. --.
-- example tumor diseases. --.

Column 57,
Line 7, should read:
-- $R_1$ is hydrogen, or lower alkyl that is unsubstituted or --.

Column 58,
Line 64, (line 4 form the bottom of the column), should read:
-- u) 4-(3-chloro-anilino)-6-(4-ethoxycarbonyl-phenyl)-7H- --.

Column 59,
Lines 1, 3 and 5, respectively, should read:
-- w) 6-(N-benzyl-carbamoyl)-4-(3-chloro-anilino)-7H-pyrrolo --.
-- x) 4-(3-chloro-anilino-6-(N-[3-methyl-but-1-yl]- --.
-- or a pharmaceutically acceptable salt thereof. --.
Line 37, (last line of claim 11), should read:
-- or a parmaceutically acceptable salt thereof --.

Column 62,
Lines 37 and 47, respectively, should read:
-- c) when q is 1, $R_1$ and $R_2$ are each independently of the --.
-- the compound of formula I wherein n is 2, q is 1, $R_1$ and $R_6$ --.

Signed and Sealed this

Fifth Day of February, 2002

Attest:

JAMES E. ROGAN
*Director of the United States Patent and Trademark Office*

*Attesting Officer*